(12) United States Patent
Nishimura et al.

(10) Patent No.: US 10,272,153 B2
(45) Date of Patent: Apr. 30, 2019

(54) ANTIBODY TO MUCIN 4 (MUC4) GLYCOPEPTIDE AND USES THEREOF

(71) Applicant: MEDICINAL CHEMISTRY PHARMACEUTICALS, Co., Ltd., Hokkaido (JP)

(72) Inventors: Shinichiro Nishimura, Hokkaido (JP); Risho Miyoshi, Hokkaido (JP); Kentaro Naruchi, Hokkaido (JP); Masakazu Tanaka, Hokkaido (JP)

(73) Assignee: MEDICINAL CHEMISTRY PHARMACEUTICALS Co., Ltd., Hokkaido (JP)

( * ) Notice: Subject to any disclaimer, the term of this patent is extended or adjusted under 35 U.S.C. 154(b) by 39 days.

(21) Appl. No.: 15/117,130

(22) PCT Filed: Feb. 5, 2015

(86) PCT No.: PCT/JP2015/053175
§ 371 (c)(1),
(2) Date: Aug. 5, 2016

(87) PCT Pub. No.: WO2015/119180
PCT Pub. Date: Aug. 13, 2015

(65) Prior Publication Data
US 2017/0173152 A1    Jun. 22, 2017

(30) Foreign Application Priority Data

Feb. 6, 2014    (JP) .................................. 2014-020869

(51) Int. Cl.
| | | |
|---|---|---|
| C07K 16/30 | (2006.01) | |
| A61K 39/395 | (2006.01) | |
| C07K 9/00 | (2006.01) | |
| G01N 33/53 | (2006.01) | |
| G01N 33/574 | (2006.01) | |
| A61K 39/00 | (2006.01) | |
| C07K 14/47 | (2006.01) | |

(52) U.S. Cl.
CPC .... *A61K 39/39558* (2013.01); *A61K 39/0011* (2013.01); *C07K 9/00* (2013.01); *C07K 16/3092* (2013.01); *G01N 33/53* (2013.01); *G01N 33/574* (2013.01); *G01N 33/57415* (2013.01); *G01N 33/57419* (2013.01); *G01N 33/57423* (2013.01); *G01N 33/57438* (2013.01); *G01N 33/57449* (2013.01); *G01N 33/57496* (2013.01); *A61K 2121/00* (2013.01); *C07K 14/47* (2013.01); *C07K 2317/34* (2013.01)

(58) Field of Classification Search
None
See application file for complete search history.

(56) References Cited

U.S. PATENT DOCUMENTS

| | | |
|---|---|---|
| 2007/0092531 A1 | 4/2007 | McKenzie et al. |
| 2012/0040375 A1 | 2/2012 | Nishimura et al. |
| 2013/0045543 A1 | 2/2013 | Nishimura et al. |

FOREIGN PATENT DOCUMENTS

| | | |
|---|---|---|
| JP | 06-113831 A | 4/1994 |
| JP | 07-206707 A | 8/1995 |
| JP | 10-276773 A | 10/1998 |
| JP | 2006-111618 | 4/2006 |
| JP | 2012-167018 A | 9/2012 |
| WO | 03/106497 A1 | 12/2003 |
| WO | 2010/050528 A1 | 5/2010 |
| WO | 2011/012309 A1 | 2/2011 |
| WO | 2011/054359 A2 | 5/2011 |
| WO | 2011/135869 A1 | 11/2011 |

OTHER PUBLICATIONS

Xing et al. (International Journal of Oncology, 11: 289-295, 1997).*
Mariuzza et al. (Annu. Rev. Biophys. Biophys. Chem., 16: 139-159, 1987).*
Extended European Search Report dated Jul. 14, 2017 in the corresponding European patent application (EP 15746770.5), filed Sep. 2, 2016.
Sukhwinder Kaur et al., "Mucins in pancreatic cancer and its microenvironment", Nature Reviews Gastroenterology & Hepatology, vol. 10, No. 10, Jul. 16, 2013, pp. 607-620.
(Continued)

*Primary Examiner* — Nelson B Moseley, II
(74) *Attorney, Agent, or Firm* — Robert C. Netter, Jr.; Dann, Dorfman, Herrell & Skillman

(57) ABSTRACT

The present invention provides: an antibody that has specificity for MUC 4 having a sugar chain structure that is expressed at a high level in cancer cells; a glycopeptide that constitutes an antigen that is suitable for producing this antibody; and a new means and method for the diagnosis, prevention, and/or treatment of cancer by means of the aforementioned antibody. The present invention relates to a monoclonal antibody against a glycopeptide. The glycopeptide comprises a human MUC 4 tandem unit peptide having an amino acid sequence represented by SEQ ID NO: 1, and an O-linked sugar chain. The O-linked sugar chain is N-acetylgalactosamine (GalNAc) and binds to threonine, which is the 8th amino acid of the tandem unit peptide. The present invention further includes: a glycopeptide for use in the production of a monoclonal antibody against human MUC 4; a method for detecting MUC 4 in a human body fluid sample; a kit that includes the abovementioned monoclonal antibody; and a pharmaceutical composition for the prevention and/or treatment of malignant tumors that contains the abovementioned monoclonal antibody as an active component.

16 Claims, 6 Drawing Sheets

Specification includes a Sequence Listing.

(56) References Cited

OTHER PUBLICATIONS

Chahaturvedi et al., Structure, evolution, and biology of the MUC4 mucin, FASEB J, 2008, 22(4):966-981.
Beatson et al., MUC1 immunotherapy, Immunotherapy, 2010, 2(3):305-327.
Singh et al., Inhibition of MUC4 expression suppresses pancreatic tumor cell growth and metastasis, Cancer Res, 2004, 64(2):622-630.
Liu and Rabinovich, Galectins as modulators of tumour progression, Nature Rev Cancer, 2005, 5(1):29-41.
Sanapati et al., Novel INTeraction of MUC4 and galectin: potential pathobiological implications for metastasis in lethal pancreatic cancer, Clin Cancer Res, 2011, 17(2):267-274.
Moniaux et al., Generation and characterization of anti-MUC4 monoclonal antibodies reactive with normal and cancer cells in humans, J Histochem Cytochem, 2004, 52(2):253-261.
Zhang et al., Presence of MUC4 in human milk and at the luminal surfaces of blood vessels, J Cellular Physiol, 2005, 204(1):166-177.
Matsushita et al., Site-specific conformational alteration induced by sialylation of MUC1 tandem repeating glycopeptides at an epitope region for the anti-KL-6 monoclonal antibody, Biochemistry, 2013, 52(2):402-414.
Hashimoto et al., An efficient approach for the characterization of mucin-type glycopeptides: the effect of O-glycosylation on the conformation of synthetic mucin peptides, Chem Eur J, 2011, 17(8)2393-2404.
Ohyabu et al., An essential epitope of anti-MUC1 monoclonal antibody KL-6 revealed by focused glycopeptide library, J Am Chem Soc, 2009, 131(47):17102-17109.
Matsushita et al., A straightforward protocol for the preparation of high performance microarray displaying synthetic MUC1 glycopeptides, Biochimica et Biophysica Acta, 2014, 1840(3):1105-1116.
Xing et al., Monoclonal Antibodies to a MUC 4 peptide react with lung cancer, International Journal of Oncology, 1997, 11:289-295.
Kim et al., Nanospray-ESI low-energy CID and MALDI post-source decay for determination of O-glycosylation sites in MUC4 peptides, Journal of Mass Spectrometry, 1998, 33(11): 1124-1133.
International Search Report and Written Opinion and Written Opinion issued in PCT/JP2015/053175.
International Preliminary Report on Patentability issued in PCT/JP2015/053175.
English version of International Preliminary Report on Patentability issued in PCT/JP2015/0531.
Examination Report cited in related EP Application No. EP 15746770.5 dated May 23, 2018.
Hollingsworth, M.A., et al., "Mucins in cancer: protection and control of the cell surface" Nat. Rev. Cancer (2004) 4(1):45-60.
Japanese Patent Office, Office Action dated Dec. 4, 2018 issued in the corresponding Japanese patent application No. 2015-561022.
Gaidzik, N., et al., "The development of synthetic antitumour vaccines from mucin glycopeptide antigens" Chem. Soc. Rev. (2013) 42(10):4421-42.
Wandall, H.H., et al., "The lectin domains of polypeptide GalNAc-transferases exhibit carbohydrate-binding specificity for GalNAc: lectin binding to GalNAc-glycopeptide substrates is required for high density GalNAc-O-glycosylation" Glycobiology (2007) 17(4):374-87.
European Patent Office, Office Action dated Mar. 7, 2019 issued in the corresponding European patent application No. 15746770.5.

* cited by examiner (A) Immobilized MUC4-derived glycopeptide array.

(B) Immobilized MUC1-derived glycopeptide array.

(C) Immobilized MUC2-derived glycopeptide array.  (D) Immobilized MUC16-derived glycopeptide array.

```
                         SEQUENCE LISTING

<160> NUMBER OF SEQ ID NOS: 5

<210> SEQ ID NO 1
    <211> LENGTH: 16
    <212> TYPE: PRT
    <213> ORGANISM: Homo Sapience

<400> SEQUENCE: 1

Ser Ala Ser Thr Gly His Ala Thr Pro Leu Pro Val Thr Asp Thr Ser
    1               5                   10                  15

<210> SEQ ID NO 2
    <211> LENGTH: 17
    <212> TYPE: PRT
    <213> ORGANISM: Homo Sapience

<400> SEQUENCE: 2

Ser Ala Ser Thr Gly His Ala Thr Pro Leu Pro Val Thr Asp Thr Ser
    1               5                   10                  15

Cys

<210> SEQ ID NO 3
    <211> LENGTH: 24
    <212> TYPE: PRT
    <213> ORGANISM: Homo Sapience

<400> SEQUENCE: 3

Gly Val Thr Ser Ala Pro Asp Thr Arg Pro Ala Pro Gly Ser Thr Ala
    1               5                   10                  15

Pro Pro Ala His Gly Val Thr Cys
                20

<210> SEQ ID NO 4
    <211> LENGTH: 19
    <212> TYPE: PRT
    <213> ORGANISM: Homo Sapience

<400> SEQUENCE: 4

Pro Pro Thr Thr Thr Pro Ser Pro Pro Pro Thr Ser Thr Thr Thr Leu
    1               5                   10                  15

Pro Pro Thr

<210> SEQ ID NO 5
    <211> LENGTH: 21
    <212> TYPE: PRT
    <213> ORGANISM: Homo Sapience
```

```
<400> SEQUENCE: 5

Val Gly Pro Leu Tyr Ser Gly Cys Arg Leu Thr Leu Arg Pro Glu
1               5                   10                  15

Leu His Gly Ala Ala
            20
```

ANTIBODY TO MUCIN 4 (MUC4) GLYCOPEPTIDE AND USES THEREOF

CROSS-REFERENCE TO RELATED APPLICATIONS

The present application is § 371 application of PCT/JP2015/053175 filed Feb. 5, 2015 which claims priority to JP Patent Application No. 2014-020869 filed Feb. 6, 2014, the entire disclosure of each being incorporated by reference herein.

TECHNICAL FIELD

The present invention relates to techniques in the field of antibodies. More particularly, the present invention relates to an antibody for mucin 4 (MUC4) glycopeptide as well as a diagnostic technique and a technique for preventing and/or treating malignant tumors employing this antibody.

BACKGROUND ART

Mucin is an important glycoprotein of the mucous that covers the trachea, the digestive tract such as the stomach, lumina such as the gonads, and the like. Mucin has countless sugar chains that are bonded to polypeptides (core proteins) through O-glycoside bonds. The core proteins of mucin are coded by various mucin genes (MUC genes). Important roles of mucin are to protect and hydrate as well as to lubricate mucous membranes. Mucin also participates in regulating the differentiation and regeneration of the epithelium, cell adhesion, the immune response, cell signaling, and the like. In recent years, numerous genes coding for many core proteins of mucin have been cloned, and their full or partial sequences have been determined. Most mucins have many repetitive sequence domains (tandem repeats). These tandem repeats are comprised of amino acid sequences (tandem units) of varying length, and are rich in serine, threonine, and proline residues. Many O-linked sugar chains of various structures are added to these serine or threonine residues. In the completed mucin, residues that are not considered to be 0-glycosylated (naked peptides) are present in a constant ratio. Generally, the sugar chains are comprised of N-acetylgalactosamine (GalNAc), N-acetylglucosamine (GlcNAc), galactose (Gal), fucose (Fuc), sialic acid (SA), mannose (Man), and the like. Mucin comes in the forms of secreted mucin that is produced by the epithelial cells and the like, and membrane-bonded mucin that has a hydrophobic transmembrane site and is present in a state bonded to cell membranes.

The core proteins of mucin are collectively referred to as mucin, with numbers being assigned in order of discovery. In humans, 19 genes coding for these core proteins have been reported (MUC1, 2, 3A, 3B, 4, 5AC, 5B, 6, 7, 8, 9, 11, 12, 13, 15, 16, 17, 18, 19). Of these, 11 are transmembrane mucin and seven are secreted mucin (Nonpatent Reference 1).

MUC4 is present in the epithelial tissue of the trachea, colon, stomach, ectocervix, lungs, and the like (Nonpatent Reference 1). MUC4 is known to be associated with various diseases, such as cancer.

The extracellular domains of human MUC4 contain various numbers of tandem units of 16 amino acid residues having seven potential O-glycosylation sites. In O-glycan, the sugars that are initially transferred to the serine and threonine residues of the core protein through O-bonds in greatest quantity are GalNAc, followed by Man, Fuc, Glc-NAc, and the like. O-glycans are incompletely processed by cancer cells, and cause the expression of common sugar antigens Tn (GalNAcα-1-Ser/Thr), STn (NeuAcα2-6 GalNAcα1-O-Ser/Thr), and T (Galβ1-3 GalNAcα-1-O-Ser/Thr) with cancer. After the initial sugar, sugars are transferred one after another and the O-glycan sugar chain grows longer. Many core structures of the O-glycan to which GalNAc is initially transferred are known and have been numbered. The main currently known core structures are indicated below. Longer sugar chains of more complex structure grow based on these structures.

Core 0 (Tn antigen) GalNAc
Core 1 (T antigen) Galβ1-3GalNAc
Core 2: Galβ1-3(GlcNAcβ1-6) GalNAc
Core 3: GlcNAcβ1-3GalNAc
Core 4: GlcNAcβ1-3(GlcNAcβ1-6) GalNAc
Core 5: GalNAcα1-3GalNAc
Core 6: GlcNAcβ1-6GalNAc
Core 7: GalNAcα1-6GalNAc
Core 8: Galα1-3GalNAc
Core 9: Galβ1-3(Galβ1-6) GalNAc
Core 10: GalNAcβ1-3GalNAc
Core 11: GalNAcβ1-3(GalNAcβ1-6) GalNAc
Core 12: Galβ1-3(Glcβ1-6) GalNAc
Core 13: Galβ1-3(Glcβ1-4) (Glcβ1-6) GalNAc The addition of sugar chains by the O-glycosylation of mucin core proteins plays important roles in the protection of the outer layer of epithelial cells, immune reactions, cell adhesion, inflammatory reactions, carcinogenesis, and cancerous metastasis. Among the mucins, much research has been conducted on MUC1 mucin. The overexpression of MUC1 in carcinogenesis and the connection between the dramatic change in O-glycosylation and carcinogenesis and metastasis have been reported. Further, research and development of diagnostic and therapeutic drugs for lung cancer and ovarian cancer employing monoclonal antibodies to MUC1 is advancing (Nonpatent Reference 2, Patent References 1 and 2).

Marked fluctuation in the expression of core proteins accompanying carcinogenesis has been reported for MUC4 (Nonpatent Reference 1). Overexpression of MUC4 in pancreatic and esophageal cancer has been found to accelerate cancer proliferation and metastasis (Nonpatent Reference 1). Additionally, by inhibiting expression of the MUC4 gene in cancer cells, the proliferation of cancer cells is markedly inhibited, and it has become clear in in vivo investigation that cell migration, cell adhesion, and aggregation are accelerated. It has been indicated that were it possible to inhibit the function of MUC4, it would be possible to impede the progress and metastasis of metastatic cancer (Nonpatent Reference 3). Further, the fact that interaction between MUC4 and galectin is important in the metastatis of pancreatic cancer and the like has been recently discovered (Nonpatent References 4 and 5).

Patent Reference 1: WO2010/050528
Patent Reference 2: WO2011/135869
Patent Reference 3: JP-A-2006-111618
Patent Reference 4: WO2011/054359
Nonpatent Reference 1: Chaturvedi et al., FASEB J. 22: 966-981 (2008)
Nonpatent Reference 2: Beatson et al., Immunotherapy 2: 305-327 (2010)
Nonpatent Reference 3: Singh et al., Cancer Res. 64: 622-630 (2004)
Nonpatent Reference 4: Liu and Rabinovich, Nature Rev. Cancer 5: 29-41 (2005)

Nonpatent Reference 5: Sanapati et al., Clin Cancer Res 17:267-274 (2011)
Nonpatent Reference 6: Moniaux et al., J. Histochem. Cytochem. 52: 253-261(2004)
Nonpatent Reference 7: Zhang et al., J. Cellular Physiol. 204: 166-177 (2005)
Nonpatent Reference 8: Matsushita et al., Biochemistry 52:402-414 (2013)
Nonpatent Reference 9: Hashimoto et al., Chem. Eur. J. 17: 2393-2404 (2011)
Nonpatent Reference 10: Ohyabu et al., J. Am. Chem. Soc. 131: 17102-17109 (2009)
Nonpatent Reference 11: Matsusita et al., Biochim. Biophy. Acta 1840: 1105-1116 (2014)
Nonpatent Reference 12: Sanapati et al., Clin Cancer Res 17:267-274 (2011)

A number of monoclonal antibodies to purified MUC4 of unspecified structure and recombinant and synthetic peptides of the MUC4 gene have been manufactured in the past. For example, a monoclonal antibody to the MUC4β, unit peptide in the form of IG8 (Nonpatent Reference 7) and a monoclonal antibody to the MUC4 tandem unit peptide STGDTTPLPVTDTSSV in the form of 8G7 (Nonpatent Reference 6) have been achieved and are employed as research tools. There are reports of monoclonal antibodies to glycopeptides derived from MUC4 in the form of 4D9, 3C9, 6E3, and 6C11 (Patent Reference 4). However, they are all antibodies with low specificity in which the sugar modification sites and numbers are not specified for the MUC4 peptide.

Accordingly, the present invention has for its object to provide an antibody specific to MUC4 having a sugar chain structure that is highly expressed in cancer cells, a glycopeptide serving as an antigen suited to the preparation of this antibody, and a new means and method of diagnosing, preventing, and/or treating cancer based on this antibody.

The present inventors demonstrated by NMR that structurally specific conformational change was induced in the main chain peptides of the sugar chains bonded to side chains in the epitope region of the antibody, that peptide conformation was sensitively changed by sugar chain modification in specific amino acid residues, and that this specified the antigen structure in the MUC1 antibody (Nonpatent Reference 8). Analysis of change in the three-dimensional structure of synthetic glycopeptides derived from mucin by MS and NMR has revealed that the conformation of glycopeptides was affected by sugar chain modification of the multiple threonine residues present in the peptide, and the new knowledge that sugar chain modification at specific sites imparted stable conformation of the peptide main chain (Nonpatent Reference 9). Additionally, the present inventors synthesized many O-linked sugar amino acids and glycopeptides, including the compounds described in (Patent Reference 3), to elucidate the various structures and functions of the sugar chains.

Further, a highly sensitive, high-performance immobilized glycopeptide microarray that is capable of accurate antibody specificity analysis and epitope mapping has been developed, and a new method of determining the true epitope structure has been established (Nonpatent References 10 and 11).

Means of Solving the Problem

The present inventors applied the new techniques and knowledge about sugar chains and glycopeptides that they obtained. In order to solve the problems set forth above, they synthesized glycopeptides of specific regions of the MUC4 that is expressed in various cancer cells and employed them as antigen to prepare monoclonal antibodies. A number of anti-MUC4 antibodies were obtained for a single antigen, antigen specificity analysis was conducted using a microarray loaded with glycopeptides derived from specific regions of various mucins containing the glycopeptides employed as antigen, and the specificity of the antibodies was examined. These antibodies were also examined for binding and accumulation to the MUC4 expressed by various cancer cells, reaction to patient blood serum, cancer cell proliferation-blocking action, metastasis-blocking action, and the like. The present invention was devised based on the results of this examination.

The present invention is as set forth below.

[1]
A monoclonal antibody to a glycopeptide,
wherein the glycopeptide comprises a tandem unit peptide of human MUC4 having the amino acid sequence given by SEQ ID NO: 1 and a O-linked sugar chain;
the O-linked sugar chain is N-acetylgalactosamine (GalNAc) and is bonded to the threonine that is the eighth amino acid in the tandem unit peptide.

[2]
A monoclonal antibody having the binding properties set forth in i) to iii) below:
i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);
ii) not binding to a peptide having the amino acid sequence denoted by SEQ ID NO:1, and to glycopeptides having the amino acid sequence denoted by SEQ ID NO:1 in which Tn is modified at a position different from the glycopeptide employed as antigen;
iii) either not binding or binding weakly to a glycopeptide in which Tn is modified with a tandem unit peptide of MUC1, MUC2, or MUC16.

[3]
The monoclonal antibody of [1] or [2], secreted by the hybridoma cell system registered under Accession Number NITE BP-01777, denoted as monoclonal antibody SN-04.

[4]
A monoclonal antibody having the binding properties set forth in i) to iv) below:
i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);
ii) not binding to a peptide having the amino acid sequence denoted by SEQ ID NO:1, and to glycopeptides having the amino acid sequence denoted by SEQ ID NO:1 in which Tn is modified at a position different from the glycopeptide employed as antigen;
iii) strongly binding to a glycopeptide in which Tn is modified with tandem unit peptides of MUC2 and MUC16; and
iv) not binding to a glycopeptide in which Tn is modified with an MUC1 tandem unit peptide.

[5]
The monoclonal antibody according to [1] or [4], secreted by the hybridoma cell system registered under Accession Number NITE BP-01774 in the form of monoclonal antibody SN-01.

[6]

The monoclonal antibody according to [1] or [4], secreted by the hybridoma cell system registered under Accession Number NITE BP-01775 in the form of monoclonal antibody SN-02.

[7]

A monoclonal antibody having the binding properties set forth in i) to iii) below:

i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);

ii) binding to both a peptide having the amino acid sequence denoted by SEQ ID NO:1, and to glycopeptides having the amino acid sequence denoted by SEQ ID NO:1 in which Tn is modified at a position different from the glycopeptide employed as antigen; and iii) not binding to a glycopeptide in which Tn is modified with a tandem unit peptide of MUC1, MUC2, or MUC16.

[8]

The monoclonal antibody according to [1] or [7], secreted by the hybridoma cell system registered under Accession Number NITE BP-01776 in the form of monoclonal antibody SN-03.

[9]

The monoclonal antibody according to any one of [1] to [8], that is for use in detection of MUC4.

[10]

A glycopeptide for preparing anti-human MUC4 monoclonal antibody, wherein the glycopeptide comprises a tandem unit peptide of human MUC4 having the amino acid sequence given by SEQ ID NO: 1 or the peptide having the amino acid sequence given by SEQ ID NO: 2 and a O-linked sugar chain;

the O-linked sugar chain is N-acetylgalactosamine (GalNAc) and is bound to the threonine that is the eighth amino acid in the tandem unit peptide.

[11]

A method for detecting MUC4 in a human body fluid sample, comprising:

(a) contacting the sample with the monoclonal antibody according to any one of [1] to [8]; and (b) measuring the formation of antibody-antigen complex in the sample after contact.

[12]

The method according to [11], that is employed to detect the presence or absence of a malignant tumor in which the abnormal expression of MUC4 is observed in the body fluid sample.

[13]

The method according to [12], in which the malignant tumor is selected from the group consisting of pancreatic cancer, ovarian cancer, breast cancer, biliary tract cancer, esophageal cancer, colon cancer, and lung cancer.

[14]

A kit for employing the method according to any one of [11] to [13], comprising:

(a) the monoclonal antibody according to any one of [1] to [8]; and (b) a reagent for measuring antibody-antigen complex.

[15]

A pharmaceutical composition for preventing and/or treating malignant tumors, containing the monoclonal antibody according to any one of [1] to [8] as an active ingredient.

[16]

The composition according to [15], wherein the malignant tumor is selected from the group consisting of pancreatic cancer, ovarian cancer, breast cancer, biliary tract cancer, esophageal cancer, colon cancer, and lung cancer.

[17]

A pharmaceutical composition for preventing and/or treating malignant tumors, comprising the monoclonal antibody according to any one of [1] to [8] and a chemotherapeutic agent or molecularly targeted drug as active ingredient.

[18]

The pharmaceutical composition according to [17], wherein the malignant tumor is selected from the group consisting of pancreatic cancer, ovarian cancer, breast cancer, biliary tract cancer, esophageal cancer, colon cancer, and lung cancer.

[19]

The pharmaceutical composition according to [17] or [18], wherein the monoclonal antibody and chemotherapeutic agent or molecularly targeted drug are employed on mutually different administration schedules.

Effect of the Invention

The present invention provides an anti-MUC4 antibody that specifically recognizes and bonds to the sugar chain core structure of antigen glycopeptides derived from MUC4, and an antigen glycopeptide for preparing the antibody. Using the anti-MUC4 antibody of the present invention, it is possible to specifically, highly sensitively, reliably, and readily detect MUC4 protein. It is also becomes possible to determine malignant tumors and inflammatory diseases in which changes in MUC4 expression relative to normal controls are observed.

It has been further shown that by suppressing the advancement and metastatis of cancer with the anti-MUC4 antibody of the present invention, the latter can be used to prevent and/or treat cancer prevention.

BRIEF DESCRIPTION OF THE DRAWINGS

FIG. 5-1 Shows an immobilized glycopeptide microarray layout and the evaluation of the reaction specificity of various antibodies. (A) Immobilized MUC4-derived glycopeptide array.

FIG. 5-2 Shows an immobilized glycopeptide microarray layout and the evaluation of the reaction specificity of various antibodies. (B) Immobilized MUC1-derived glycopeptide array. (C) Immobilized MUC2-derived glycopeptide array. (D) Immobilized MUC16-derived glycopeptide array.

MODES OF CARRYING OUT THE INVENTION

Figure 1:
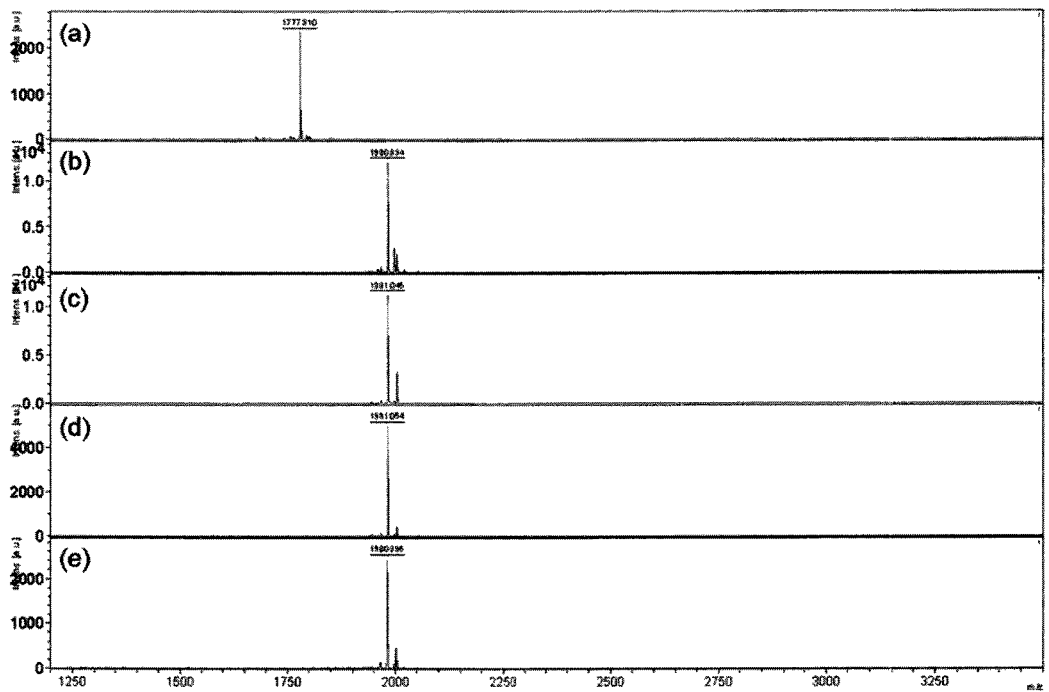
FIG. 1 The MALDI-TOFMS spectrum of an MUC4-derived glycopeptide.

The present invention will be described in greater detail below.

1. Antigen Glycopeptide and Antibodies

The antibodies relating to the present invention are monoclonal antibodies to the glycopeptide set forth below.

The glycopeptide is comprised of a tandem unit peptide of human MUC4 having the amino acid sequence given by SEQ ID NO: 1 and an O-linked sugar chain.

The O-linked sugar chain is N-acetylgalactosamine (GalNAc) and is bonded to the threonine that is the eighth amino acid in the tandem unit peptide.

1-1. The Antigen Glycopeptide

"MUC4" is a type of mucin glycoprotein. The transmembrane form of MUC4 is thought to contribute to protecting the outer surface of the cell and the secreted form is thought to have a lubricating effect and to play a part in protecting the lumen surface by capturing foreign matter and pathogens. MUC4, which codes for the core protein of MUC4, has been cloned from a cDNA library of human tracheobronchial mucosa and a pancreatic cancer cell strain (Nonpatent Reference 1). The molecular size of the MUC4 core protein is from 550 to 930 kDa and is comprised of the three regions of a short N-terminal region, a middle region comprised of a repeating series of amino acids, and a C-terminal region. The C-terminal region is comprised of 12 domains in the form of CT-1 to CT12 contributing to the various functions of MUC4. There is a transmembrane domain and a short cytoplasmic tail. The giant extracellular unit containing the N-terminal domain, the middle domain, and part of the C-terminal is divided into MUC4α subunits, and the C-terminal unit containing the cell cytoplasmic tail and the rest of the transmembrane domain is divided into MUC4β subunits. Human MUC4 is characteristically in the form of tandem units comprised of 16 amino acids.

The tandem unit peptide of human MUC4 having the amino acid sequence given by SEQ ID NO: 1 has the following amino acid sequence (SEQ ID NO: 1).

Ser-Ala-Ser-Thr-Gly-His-Ala-Thr-Pro-Leu-Pro-Val-Thr-Asp-Thr-Ser

However, in antibody preparation, to bind this tandem unit peptide to a carrier protein, a glycopeptide comprised of the glycopeptide to which Cys has been added that is indicated below (SEQ ID NO: 2) and an O-linked sugar chain was employed as antigen.

Ser-Ala-Ser-Thr-Gly-His-Ala-Thr-Pro-Leu-Pro-Val-Thr-Asp-Thr-Ser-Cys

The O-linked sugar chain is N-acetylgalactosamine (GalNAc). The O-linked sugar chain is bonded to the threonine (Thr) that is the eighth amino acid in the above tandem unit peptide.

The peptide (SEQ ID NO: 1) having N-acetylgalactosamine (GalNAc) bonded to the eighth threonine (Thr) is shown in (a) below. The same applies to the peptide of SEQ ID NO: 2.

(a) Ser-Ala-Ser-Thr-Gly-His-Ala-(Tn)Thr-Pro-Leu-Pro-Val-Thr-Asp-Thr-Ser

The synthesis of antigen glycopeptides is conducted by a synthesis technique utilizing the microwave and enzyme synthesis methods and the glycoblotting method to a high degree, that are those developed by the present inventors. More particularly, for example, it can be implemented based on the methods described in Nonpatent Reference 11 and Patent References 1 to 3. Synthesis examples are described in detail in Example 1.

1-2. The Antibodies

The antibodies of the present invention are prepared by the usual methods employing the above glycopeptide as antigen.

An anti-MUC4 monoclonal antibody can be prepared using antigen glycopeptide synthesized by the method set forth in the examples. It is possible to conduct binding to a carrier protein in order to heighten the antigenic property. In that case, a glycopeptide to which the Cys required for bonding the carrier protein to the glycopeptide has been added is synthesized and employed as the antigen glycopeptide. Carrier proteins can be keyhole limpet hemocyanin (KLH), bovine serum albumin (BSA), ovalbumin (OVA), or the like. Commercial kits that are known in the technical field and are also commercially available. The antigen is administered to a mammal, such as a mouse, rabbit, or rat. Immunization is primarily conducted by intravenous, subcutaneous, intraperitoneal, and footpad injection. The immunization interval is not specifically limited; one to five injections can be made at intervals of several days to several weeks. Antibody-producing cells are collected from several days to 90 days after the last immunization. Examples of antibody-producing cells are lymph node cells, spleen cells, peripheral blood cells and the like. To obtain hybridomas, antibody-producing cells and myeloma cells are fused. Commonly available cell strains can be employed as myeloma cells. It is desirable to employ cells that have the properties of drug selectivity, inability to grow on HAT selective medium (containing hypoxanthine, aminopterin, and thymidine) in an unfused state, and the ability to survive only in a state fused with an antibody-producing cell. Examples of myeloma cells are SP2, P3X63-Ag.8.UI (P3UI), and NS-1.

The targeted hybridomas are screened from the cells following cell fusion. For example, a cell suspension is suitably diluted with RPM-1640 medium containing bovine fetal serum, and then seeded onto a microtiter plate. A selective medium (such as HAT) is added to each well, and the selective medium is then suitably replaced to culture the cells. As a result, after beginning the cultures with selective medium, the cells that begin to grow in about 10 to 30 days can be obtained as hybridomas. Next, the supernatant of the hybridoma supernatant is screened with enzyme-linked immunosorbent assay (ELISA) or the like to determine whether antibodies reacting with MUC4 are present. The fused cells are screened by the limiting diluting method or the like to establish hybridomas producing the targeted monoclonal antibody.

The usual cell culturing methods, ascites forming methods or the like can be adopted to collect the monoclonal antibody from the hybridomas that have been established. The antibody can be purified by suitably selecting a known method such as ammonium sulfate precipitation, ion-exchange chromatography, gel filtration, affinity chromatography, or some combination thereof.

The globulin type of the monoclonal antibodies that can be used in the present invention is not specifically limited. IgG, IgM, IgA, IgE, or IgD will do, and IgG and IgM are preferred.

The anti-MUC4 monoclonal antibodies of the present invention are mouse antibodies. However, they can be converted into chimeric antibodies, humanized antibodies, or fully human antibodies by several known techniques that have been established.

Specific examples of the monoclonal antibodies of the present invention are SN-01 to SN-04, which are described in the examples. These monoclonal antibodies are secreted by the hybridoma cell systems deposited under Accession Numbers NITE BP-01774 to NITE BP-01777 on 5 Dec. 2013 with the Patent Microorganism Depositary (NPMD), National Institute of Technology and Evaluation (NITE), (2-5-8 Kazusakamatari, Kisarazu-shi, Chiba Prefecture, Japan, Postal Code 292-0818).

Monoclonal antibody SN-01 has the binding properties of i) to iv) below:
 i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, where Tn denotes a O-linked sugar chain comprised of N-acetylgalactosamine (GalNAc);
 ii) not binding to a peptide (naked peptide) having the amino acid sequence denoted by SEQ ID NO:1, and to glycopeptides having the amino acid sequence denoted by SEQ ID NO:1 in which Tn is modified at a different position from the glycopeptide employed as antigen;
 iii) strongly binding to a glycopeptide in which Tn is modified with tandem unit peptides in the form of MUC2 and MUC16; and
 iv) not binding to a glycopeptide in which Tn is modified with an MUC1 tandem unit peptide.

Monoclonal antibody SN-02 has the binding properties of i) to iv) below:
 i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, where Tn denotes a O-linked sugar chain comprised of N-acetylgalactosamine (GalNAc);
 ii) not binding to a peptide (naked peptide) having the amino acid sequence denoted by SEQ ID NO:1, and to glycopeptides having the amino acid sequence denoted by SEQ ID NO:1 in which Tn is modified at a different position from the glycopeptide employed as antigen;
 iii) binding to a glycopeptide in which Tn is modified with tandem unit peptides in the form of MUC2 and MUC16; and
 iv) not binding to a glycopeptide in which Tn is modified with an MUC1 tandem unit peptide.

Monoclonal antibody SN-03 has the binding properties of i) to iii) below:
 i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, where Tn denotes a O-linked sugar chain comprised of N-acetylgalactosamine (GalNAc);
 ii) binding to both a peptide (naked peptide) having the amino acid sequence denoted by SEQ ID NO:1, and to glycopeptides having the amino acid sequence denoted by SEQ ID NO:1 in which Tn is modified at a different position from the glycopeptide employed as antigen; and
 iii) not binding to a glycopeptide in which Tn is modified with a tandem unit peptide in the form of MUC1, MUC2, or MUC16.

Monoclonal antibody SN-04 has the binding properties of i) to iii) below:
 i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, where Tn denotes a O-linked sugar chain comprised of N-acetylgalactosamine (GalNAc);
 ii) not binding to a peptide (naked peptide) having the amino acid sequence denoted by SEQ ID NO:1, and to glycopeptides having the amino acid sequence denoted by SEQ ID NO:1 in which Tn is modified at a different position from the glycopeptide employed as antigen;
 iii) either not binding or binding weakly to a glycopeptide in which Tn is modified with a tandem unit peptide in the form of MUC1, MUC2, or MUC16.

2-1. Method of Detecting MUC4 in Human Body Fluid Sample

The present invention includes a method of detecting MUC4 in a human body fluid sample. This method comprises steps (a) and (b) below:
 (a) contacting the sample with a monoclonal antibody of the present invention as set forth above; and
 (b) measuring the formation of antibody-antigen complex in the sample after contact.

2-2. Kit for Immunologically Measuring Human MUC4

The kit of the present invention is for use in the method of detecting human MUC4 of the present invention and comprises:
 (a) a monoclonal antibody of the present invention; and
 (b) a reagent for measuring an antibody-antigen complex.

The monoclonal antibody of the present invention (also referred to as "anti-MUC4 antibody") that is employed in this kit can be immobilized on a support. The support can be any substance to which an antigen will adhere that is known to a person having ordinary skill in the art. For example, the support can be the test wells of a microtiter plate, nitrocellulose, or some other suitable membrane. Alternatively, the support can be beads or a disk (such as glass, fiberglass, latex, or a plastic material such as polystyrene or polyvinyl chloride). The support can also be magnetic particles or a fiber optic sensor.

The anti-MUC4 antibody of the present invention can be labeled with a radioisotope, enzyme, fluorescent material, luminescent material, or a metal colloid, colored latex, or the like that is visually determinable by a simple measurement method. Radioisotopes that can be used for labeling are: $^{14}C$, $^{3}H$, $^{32}P$, $^{125}I$, $^{131}I$, and the like. $^{125}I$ is particularly suitable for use. This can be bonded to the monoclonal antibody by the chloramine T method, peroxidase method, iodogen method, Bolton-Hunter method, or the like. Examples of enzymes that can be employed as labels are β-galactosidase (βGAL), alkaline phosphatase (ALP), and horse radish peroxidase (HRP). These can be bonded to the monoclonal antibody by the usual methods. Florescent materials that can be employed as labels include fluorescein, fluorescamine, fluorescein isothiocyanate, and tetramethylrhodamine isothiocyanate. Luminescent materials that can be employed as labels include: luciferin, luminol derivatives, and acridinium esters. Gold colloid and colored latex can be employed in simple detection methods.

Reagents for measuring antibody-antigen complexes can be suitably determined based on the immunological detection method being employed. Known reagents capable of detecting antibody-antigen complexes that are formed when human MUC4 is contained in a human body fluid sample can be employed.

In the present invention, the term "human body fluid sample" is a material that potentially contains human MUC4, such as human blood plasma, serum, blood, urine, saliva, or a cancer tissue secretion.

Other than employing the monoclonal antibody of the present invention as antibody, the detection method of the present invention can be implemented using conventionally known immunological measurement methods. Examples of conventionally known immunological measurement methods are the immunohistochemical staining method, immunoelectron microscopy, and immunoassays (such as enzymatic immunoassays (ELISA, EIA), fluorescent immunoassays, radioimmunoassays (RIA), immunochromatography, the immunoagglutination method, and the Western blotting method). The method for measuring the formation of antibody-antigen complex in the sample following contact in step (b) can be suitably selected based on the immunological measurement method.

The immunological measurement method will be described in greater detail. An example is a sandwich immunological measurement method comprising a step of immobilizing the monoclonal antibody (first monoclonal antibody) of the present invention on a solid phase and incubating it with a sample containing antigen; a step of adding a labeled second monoclonal antibody and incubating the mixture obtained; and a step of detecting the labeled antigen-antibody complex that has been produced in the mixture. In the immunological measurement method of the present invention, the sample, immobilized first monoclonal antibody, and labeled second monoclonal antibody can be simultaneously incubated. Any sandwich immunological measurement method such as the sandwich radioimmunoassay (RIA), sandwich enzymatic immunoassay (EIA), sandwich fluorescent immunoassay (FIA), sandwich luminescence immunoassay method (CLIA), sandwich luminescence enzymatic immunoassay (CLEIA), and sandwich assay-based immunochromatography can be applied as the sandwich immunological measurement method depending on the detection method. The RIA and EIA methods are desirable for quantification.

The sandwich RIA method can be conducted based on a desirable embodiment. In the sandwich RIA method, specifically, beads on which a first monoclonal antibody (the monoclonal antibody of the present invention) has been immobilized are admixed to a standard solution or sample and the mixture is incubated for from 1 to 4 hours, desirably 2 hours, at from 4 to 45° C., desirably 25 to 37° C. (first reaction). After cleaning, a solution containing a second monoclonal antibody that has been labeled with $^{125}$I for example is added and the mixture is incubated for from 1 to 4 hours, desirably 2 hours, at from 4 to 45° C., desirably 25 to 37° C. (second reaction). Following cleaning, the radioactivity of the antigen-antibody complex that has bound to the beads is detected with a gamma counter or the like to measure a quantity. In another desirable implementation mode, the sandwich EIA method is conducted. In the sandwich EIA method, specifically, beads on which a first monoclonal antibody has been immobilized are admixed with a labeled solution or sample, and the mixture is incubated for from 1 to 4 hours, desirably 2 hours, at from 4 to 45° C., desirably 25 to 37° C. (first reaction). Following cleaning, a solution containing a second monoclonal antibody labeled with an enzyme label such as horse radish peroxidase (HRP) is added and the mixture is incubated for from 1 to 4 hours, desirably 2 hours, at from 4 to 45° C., desirably 25 to 37° C. (first reaction) and an immune complex comprised of antibody-antibody is formed on the beads (second reaction). The enzymatic activity on the beads is measured with a substrate specific to the enzyme and, for example, when the enzyme label is HRP, measured by the colorimetric method by means of tetramethylbenzidine (TMB). The quantity captured on the beads can thus be measured. Colorimetric quantification can be conducted with the usual spectrophotometer.

2-3. Detection of Human MUC4

The method of the present invention can be used to detect the presence of a malignant tumor for which abnormal MUC4 expression is observed in a body fluid sample. Examples of malignant tumors for which the abnormal expression of MUC4 is observed are those selected from the group consisting of pancreatic cancer, ovarian cancer, breast cancer, biliary tract cancer, esophageal cancer, colon cancer, and lung cancer. As set forth above, the antibody of the present invention is effective in detecting malignant tumors related to human MUC4, such as pancreatic cancer, ovarian cancer, breast cancer, biliary tract cancer, esophageal cancer, colon cancer, and lung cancer, because it reacts specifically with MUC4.

The abnormal expression of MUC4 has been reported for malignant tumors in the colon, pancreas, breasts, ovaries, and the like. MUC4 is not expressed by the healthy pancreas or in chronic pancreatitis, but its expression is seen in most pancreatic cancers and pancreatic cancer cell strains. Similarly, MUC4 is expressed by hyperplastic pancreatic ducts, and its expression increases in highly malignant intraepithelial tumors. The expression of MUC4 is stimulated relative to healthy tissue and cells in ovarian cancer, lung cancer, biliary tract cancer, highly malignant esophageal dysplasia, and esophageal cancer (Nonpatent Reference 1).

In healthy epithelial tissue, O-sugar chain modification in the VNTR region of MUC4 normally consists of polylactosamine long-chain and branched-chain sugars contain 8 to 10 monosaccharide units. Since the extracellular region of normal MUC4 is modified by such large numbers of sugar chains, it exhibits a protecting, hydrating, and lubricating effect on mucosa; a protecting effect from attacks by bacteria and foreign matter; and a regulating effect between cells and on cell matrix interaction. Further, MUC4 is expressed at the cell apex in healthy cells. However, apical expression disappears in cancer cells, becoming nonpolar expression, with MUC4 appearing over the entire cell surface. When that happens, the pattern of O-sugar chain modification in the VNTR region changes drastically, with O-sugar chain modification by simple short sugar chains appearing instead of the complex sugar chains comprised of the long chains and branched chains seen in normal cells. The low sugar-chain modification and nonpolar expression of MUC4 accompanying the development of cancer is caused by exposure of the normal cryptic peptide epitope and the creation of a new carbohydrate epitope. Accordingly, the antibodies of the present invention, which react specifically with these epitopes of MUC4, are able to distinguish between and recognize healthy and cancerous MUC4, and can be used to detect malignant tumors associated with human MUC4. It also becomes possible to attack just MUC4 that is positive for cancer cells.

The immunological measurement kit of the present invention contains the above-described anti-MUC4 antibodies. Accordingly, the kit of the present invention can be used to detect human MUC4 that is contained in a sample collected from a specimen suspected of being impeded by or afflicted with disease and thus to rapidly and readily determine the presence of an impediment or disease in the specimen. Reagents for determining disease or impediments that employ such immunological measurement methods are widely known. A person having ordinary skill in the art will be able to readily select suitable components other than antibodies. So long as the immunological measurement kit of the present invention is a technique for implementing an immunological measurement method, it can be used as part of any method.

The present invention also provides a method for diagnosing cancer employing the antibodies of the present invention, a diagnostic agent containing the antibodies of the present invention, and a diagnostic kit containing antibodies. The antibodies that are contained in the method for diagnosing cancer, diagnostic agent, and diagnostic kit of the present invention are the antibodies of the present invention as set forth above. The antibodies of the present invention can be used in these diagnoses of cancer because they specifically bind to the specific cancers set forth above.

The antibodies of the present invention can be used as markers for diagnosing the above malignant tumors and for monitoring the progress of disease in patients. In one implementation mode, cancer in a patient can be diagnosed by comparing and evaluating a biological sample obtained from a patient relative to a cutoff value determined in advance based on the MUC4 level.

Measurement results obtained by (b) above and measurement results obtained by the same steps (a) and (b) for a control sample can be compared and used to detect whether a malignant tumor is present in the body fluid sample that has been measured. The control sample can be a body fluid sample obtained from a healthy person.

To determine whether or not cancer is present, a signal detected from a reporter group binding to and remaining on a solid phase support is generally compared to the signal corresponding to a predetermined cutoff value. In one implementation mode, the cutoff value is the average value of a signal obtained by incubating immobilized antibodies along with a sample from a patient without cancer. Generally, a sample is considered to be positive for cancer when it generates a signal exceeding the predetermined cutoff value by three standard deviations. The cutoff value can be determined for example from a plot of a set of the ratio of false positives (100%-specificity) and the ratio of true positives (that is, sensitivity) corresponding to the respective possible cutoff values of diagnostic test results. The cutoff value that is closest to the upper left edge of the plot (that is, the value containing the greatest region) is the most accurate cutoff value. A sample that produced a signal that was higher than the cutoff value determined by the method of the present invention would then be considered to be positive. Alternatively, the cutoff value could either be shifted along with the plots to the left in the plot to minimize the ratio of false positives, or shifted to the right to minimize the ratio of false negatives. Generally, a sample producing a signal higher than the cutoff value determined by this method would be considered to be positive for cancer.

3. The Pharmaceutical Composition

The pharmaceutical composition of the present invention contains monoclonal antibodies as an active ingredient, is for preventing and/or treating malignant tumors, and can contain any pharmaceutically acceptable support. The malignant tumor is selected from the group consisting of pancreatic cancer, ovarian cancer, breast cancer, biliary tract cancer, esophageal cancer, colon cancer, and lung cancer.

The anti-MUC4 antibodies of the present invention can be used to prevent and/or treat diseases involving MUC4. Diseases involving MUC4 include malignant tumors such as pancreatic cancer, ovarian cancer, breast cancer, biliary tract cancer, esophageal cancer, colon cancer, and lung cancer. In patients with these malignant tumors, abnormality in the expression of MUC4, abnormality in the sugar chain structure of MUC4, and resulting functional abnormalities are recognized. Thus, the anti-MUC4 antibodies of the present invention can prevent and/or treat malignant tumors through the effects of suppressing malignant tumors.

The anti-MUC4 antibodies of the present invention can prevent and/or treat cancers by suppressing the enhanced cell proliferation caused by abnormalities and the metastasis of cancer cells in pancreatic cancer, ovarian cancer, breast cancer, biliary tract cancer, esophageal cancer, colon cancer, and lung cancer in which MUC4 expression abnormalities, abnormalities in the sugar chain structure of MUC4, and resulting functional abnormalities are observed.

Recently, the interaction between MUC4 and galectin has been found to be important in the metastasis of pancreatic cancer and the like. In the course of cancer cell invasion and metastasis, the cancer cells leave the initial site, invade the surrounding extracellular matrix and endothelial cells, and penetrate blood and lymph vessels. Ultimately, they attach at secondary sites and proliferate. The transmigration of cancer cells from circulation to metastatic sites includes (i) the stopping of circulating cancer cells and transient weak contact (docking) between cancer cells and blood vessel endothelial cells; (ii) inducing local change and ligand expression with various adhesion receptors (integrin, cadherin, and the like), and subsequently (iii) strong adhesion (locking on) of cancer cells to blood vessel endothelial cells. The interaction of MUC4 and galectin 3 has come to be understood to play an important role in these three processes. Galectins are a general term for proteins that recognize the (3-galactoside structure and bind to or crosslink sugar chains. Galectin 3 is one of 15 galectins and is known to be present in endothelial cells and in the cytoplasm and nuclei, on the surface, and in the extracellular matrix and the like of immune cells. Nonpatent Reference 12 demonstrates that the MUC4 of cancer cells binds to galectin 3, that the blood concentration of galectin 3 in patients with metastatic cancers increases relative to healthy controls, that the adhesion of circulating cancer cells to vascular endothelial cells depends on the expression of MUC4 by cancer cells and the presence of extracellular galectin 3 in epithelial cells, that the binding of extracellular galectin 3 to cancer cell MUC4 causes marked local change on the cell surface of MUC4, strengthening the bonds between cancer cells and vascular endothelial cells, and the like. It also shows that the interaction between galectin in the blood and MUC4 is an important basic molecular mechanism in the metastasis of cancer cells into distant organs. Accordingly, were it possible to block the binding of MUC4 and galectin 3, it would conceivably be possible to inhibit all of above metastatic processes (i) to (iii) and suppress metastasis.

In the examples given farther below, the antibodies of the present invention are described as blocking the binding of MUC4 and galectin 3. This suggests that using the antibodies of the present invention, it would be possible to prevent and/or treat the metastasis of cancer that overexpresses MUC4 in the development of cancers such as pancreatic cancer, ovarian cancer, and lung cancer.

The anti-MUC4 monoclonal antibodies of the present invention are mouse antibodies. The antibodies employed in the pharmacological composition of the present invention are desirably mouse antibodies that have been converted into chimeric antibodies, humanized antibodies, or fully human antibodies. Mouse antibodies can be converted into chimeric antibodies, humanized antibodies, or full human antibodies using known methods.

The pharmacological composition of the present invention can be formulated by methods known to persons having ordinary skill in the art with active ingredients in the form of the antibodies of the present invention. For example, it can be used parenterally in the form of a sterile solution in water or some other pharmaceutically acceptable liquid, or as the injection of a suspension. For example, formulation is conceivable by suitable combination with a pharmaceutically acceptable support or medium, specifically, sterile water, physiological saline, a vegetable oil, an emulsifier, a suspension agent, a surfactant, a stabilizer, a flavoring agent, an excipient, a vehicle, a preservative, a binder, or the like and mixing in the unit dose form required by generally recognized formulations. The quantity of the active ingredient in these formulations is determined so as to yield a suitable dose within the indicated range.

A sterile composition for injection can be formulated according to the usual formulations employing a vehicle such as injection-use distilled water. Examples of injection-use aqueous solutions are physiological saline and isotonic solutions containing glucose or some other adjuvant, such as D-sorbitol, D-mannose, D-mannitol, sodium chloride. For example, suitable solubilizing agents such as alcohols, specifically, ethanol and polyalcohols such as propylene glycol and polyethylene glycol, and nonionic surfactants such as polysorbate 80™ and HCO-6, can be used in combination.

Examples of oily liquids are sesame oil and soybean oil; solubilizing agents in the form of benzyl benzoate and benzyl alcohol can be employed in combination. Buffers such as phosphate buffers, sodium acetate buffers; soothing agents such as procaine hydrochloride; stabilizers such as benzyl alcohol and phenol; and oxidation inhibitors can also be formulated. The injection that is prepared is normally loaded into a suitable ampule. For delivery to cells, liposomes can be used to encapsulate the drug.

Administration can be oral or parenteral. Parenteral administration is desirable. Specific examples are injections, nasally administered agents, agents administered through the lungs, and transdermal administration. Examples are systematic or local administration in the form of an injection such as an intravenous injection, intramuscular injection, intraperitoneal injection, or subcutaneous injection.

The dose and administration method of the antibodies of the present invention can be suitably selected based on the patient's age, weight, and sex; the nature of the symptoms being treated; their severity; and the like. By way of example, a single dose of the pharmaceutical composition containing the antibodies can be selected within a range of from 0.0001 mg to 1,000 mg per kg of body weight. Alternatively, the dosage administered can be selected from within a range of from 0.01 to 100,000 mg/body of the patient. However, these numbers are not necessarily limits. The dose administered and the method of administration can be suitably varied based on the patient's age, weight, sex, symptoms, and the like. A person having ordinary skill in the art will be able to make a suitable selection.

Another embodiment of the pharmaceutical composition of the present invention is a composition for preventing and/or treating malignant tumors containing active ingredients in the form of the antibodies of the present invention and a chemotherapeutic agent or molecularly targeted drug. When employing the antibodies of the present invention in combination with a chemotherapeutic agent or molecularly targeted drug, the chemotherapeutic agent intensifies the suppression effect on the malignant tumor. When employing the pharmaceutical composition of the present invention in combination with a chemotherapeutic agent or molecularly targeted drug, it is possible to reduce the dose of the chemotherapeutic agent, reduce side effects without reducing the effect of the chemotherapeutic agent or molecularly targeted drug, and broaden the treatment concentration range. The antibodies of the present invention and the chemotherapeutic agent or molecularly targeted rug can be administered all at once or separately. When separately administered (in the case where mutually different administration schedules are employed), they can be administered continuously without break or administered at prescribed intervening intervals.

The chemotherapeutic agents and molecularly targeted drugs that can be employed in combination with the antibodies of the present invention in the pharmaceutical composition of the present invention are not specifically limited. Examples are: ifosfamide, cyclophosphamide, dacarbazine, temozolomide, nimustine, busulfan, melphalan, enocitabine, capecitabine, carmofur, cladribine, gemcitabine, cytarabine, tegafur, tegafur-uracil, TS-1, doxifluridine, nelarabine, hydroxycarbazide, fluorouracil, fludarabine, pemetrexed, pentostatin, mercaptopurine, methotrexate, irinotecan, etoposide, eribulin, sobuzoxane, docetaxel, nogitekan, paclitaxel, vinorelbine, vincristine, vindesine, vinblastine, actinomycin D, aclarubicin, amrubicin, idarubicin, epirubicin, zinostatin stimalamer, daunorubicin, doxorubicin, pirarubicin, bleomycin, peplomycin, mitomycin C, mitoxantrone, oxaliplatin, carboplatin, cisplatin, nedaplatin, anastrozole, exemestane, ethinyl estradiol, chlormadinone, goserelin, tamoxifen, dexamethasone, bicalutamide, toremifene, flutamide, prednisolone, fosfestrole, mitotane, methyltestosterone, leuprorelin, letrozole, methyl medroxyprogestrone, mepiostatin, ibritumomab tiuxetan, imatinib, everolimus, erlotinib, gefitinib, sunitinib, cetuximab, sorafenib, dasatinib, tamibarotene, trastuzumab, tretinoin, panitumumab, bevacizumab, bortezomib, and lapatinib.

The combined dose of the antibodies of the present invention and the chemotherapeutic agent and molecularly targeted drug in the pharmaceutical preposition of the present invention is not specifically limited. As set forth above, the dose of the antibodies of the present invention can be determined by referring to the dose when the antibodies are employed alone. The chemotherapeutic agent and molecularly targeted drug can be employed according to the doses indicated for the respective drugs or by reducing them (taking into account the combined effect with the antibodies of the present invention).

EXAMPLES

The present invention will be described in greater detail below through examples. However, the present invention is not limited to these examples.

Glycopeptide Synthesis

The method of synthesizing glycopeptides for evaluating the specificity of the antibodies is given below. A compound with a sequence linked to a crosslinking ketone for use in specificity evaluation, and Cys in Compounds 1 to 9, was synthesized for each compound.

Synthesis of 5-oxohexanoyl-Ser-Ala-Ser-Thr-Gly-His-Ala-Thr-Pro-Leu-Pro-Val-Thr-Asp-Thr-Ser-Cys-$NH_2$ (Compound 1)

A peptide solid phase was synthesized using a solid phase support in the form of TentaGel S RAM resin (0.24 mmol/g, 200 mg, 48 µmol, obtained from Rapp Polymere, GmbH). The amino acid extension reaction was conducted under conditions of microwave irradiation (40 W, 2,450 MHz, 50° C.) by reacting Fmoc amino acid derivative (192 µmol), HBTU (192 µmol), HOBt (192 µmol) and DIEA (288 µmol) in a DMF solution for six minutes. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was purified by reverse-phase high-performance liquid chromatography, yielding Compound 1 in the form of a freeze-dried powder (9.0 mg, yield 11%).

Synthesis of 5-oxohexanoyl-Ser-Ala-Ser-Thr(Tn)-Gly-His-Ala-Thr-Pro-Leu-Pro-Val-Thr-Asp-Thr-Ser-Cys-N $H_2$ (Compound 2)

A glycopeptide solid phase was synthesized using a solid phase support in the form of TentaGel S RAM resin (0.24 mmol/g, 100 mg, 24 µmol). The amino acid extension reaction was conducted under conditions of microwave irradiation (40 W, 2,450 MHz, 50° C.) by reacting Fmoc amino acid derivative (96 µmol), HBTU (96 µmol), HOBt (96 µmol) and DIEA (144 µmol) in a DMF solution for six minutes. The sugar chain substitution amino acid extension reaction was conducted by reacting Fmoc-Thr(Ac3GalNacα)-OH:N-α-Fmoc-O-(2-acetamide-2-deoxy-3,4,6-tri-O-acetyl-α-D-galactopyranosyl)-L-threonine (29 µmol), HBTU (29 µmol), and HOBt (29 µmol) and DIEA (72 µmol) in a DMF solution for 10 minutes with microwave irradiation. HBTU (29 µmol) and HOBt (29 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 2 in the form of a freeze-dried powder (6.4 mg, yield 14%).

Synthesis of 5-oxohexanoyl-Ser-Ala-Ser-Thr-Gly-His-Ala-Thr-Pro-Leu-Pro-Val-Thr(Tn)-Asp-Thr-Ser-Cys-$NH_2$ (Compound 4)

A glycopeptide solid phase was synthesized using a solid phase support in the form of TentaGel S RAM resin (0.24 mmol/g, 100 mg, 24 µmol). The amino acid extension reaction was conducted under conditions of microwave irradiation (40 W, 2,450 MHz, 50° C.) by reacting Fmoc amino acid derivative (96 µmol), HBTU (96 µmol), HOBt (96 µmol) and DIEA (144 µmol) in a DMF solution for six minutes. The sugar chain substitution amino acid extension reaction was conducted by reacting Fmoc-Thr(Ac3GalNacα)-OH (29 µmol), HBTU (29 µmol), and HOBt (29 µmol) and DIEA (72 µmol) in a DMF solution for 10 minutes with microwave irradiation. HBTU (29 µmol) and HOBt (29 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 4 in the form of a freeze-dried powder (10.0 mg, yield 21%).

Synthesis of 5-oxohexanoyl-Ser-Ala-Ser-Thr-Gly-His-Ala-Thr-Pro-Leu-Pro-Val-Thr-Asp-Th(Tn)r-Ser-Cys-$NH_2$ (Compound 5)

A glycopeptide solid phase was synthesized using a solid phase support in the form of TentaGel S RAM resin (0.24 mmol/g, 100 mg, 24 µmol). The amino acid extension reaction was conducted under conditions of microwave irradiation (40 W, 2,450 MHz, 50° C.) by reacting Fmoc amino acid derivative (96 µmol), HBTU (96 µmol), HOBt (96 µmol) and DIEA (144 µmol) in a DMF solution for six minutes. The sugar chain substitution amino acid extension reaction was conducted by reacting Fmoc-Thr(Ac3GalNacα)-OH (29 µmol), HBTU (29 µmol), and HOBt (29 µmol) and DIEA (72 µmol) in a DMF solution for 10 minutes with microwave irradiation. HBTU (29 µmol) and HOBt (29 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 4 in the form of a freeze-dried powder (14.4 mg, yield 31%).

Synthesis of 5-oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-Cys-NH$_2$ (Compound 6)

A peptide solid phase was synthesized using a solid phase support in the form of TentaGel S RAM resin (0.24 mmol/g, 50 mg, 12 µmol). The amino acid extension reaction was conducted under conditions of microwave irradiation (40 W, 2,450 MHz, 50° C.) by reacting Fmoc amino acid derivative (48 µmol), HBTU (48 µmol), HOBt (48 µmol) and DIEA (72 µmol) in a DMF solution for six minutes. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was purified by reverse-phase high-performance liquid chromatography, yielding Compound 1 in the form of a freeze-dried powder (6.3 mg, yield 22%).

Synthesis of 5-oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-Cys-NH$_2$ (Compound 7)

A glycopeptide solid phase was synthesized using a solid phase support in the form of TentaGel S RAM resin (0.24 mmol/g, 100 mg, 36 µmol). The amino acid extension reaction was conducted under conditions of microwave irradiation (40 W, 2,450 MHz, 50° C.) by reacting Fmoc amino acid derivative (144 µmol), HBTU (144 µmol), HOBt (144 µmol) and DIEA (216 µmol) in a DMF solution for six minutes. The sugar chain substitution amino acid extension reaction was conducted by reacting Fmoc-Thr(Ac3GalNacα)-OH (43 µmol), HBTU (43 µmol), and HOBt (43 µmol) and DIEA (108 µmol) in a DMF solution for 10 minutes with microwave irradiation. HBTU (43 µmol) and HOBt (43 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 2 in the form of a freeze-dried powder (13.3 mg, yield 15%).

Synthesis of 5-oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-Cys-NH$_2$ (Compound 8)

A glycopeptide solid phase was synthesized using a solid phase support in the form of TentaGel S RAM resin (0.24 mmol/g, 200 mg, 48 µmol). The amino acid extension reaction was conducted under conditions of microwave irradiation (40 W, 2,450 MHz, 50° C.) by reacting Fmoc amino acid derivative (192 µmol), HBTU (192 µmol), HOBt (192 µmol) and DIEA (288 µmol) in a DMF solution for six minutes. The sugar chain substitution amino acid extension reaction was conducted by reacting N-α-Fmoc-O-[2',3',4',6'-tetra-O-acetyl-D-galactopyranosyl-β(1→3)-2-acetamide-2-deoxy-4,6-di-O-acetyl-α-D-galactopyranosyl]-L-threonine (58 µmol), HBTU (58 µmol), and HOBt (58 µmol) and DIEA (144 µmol) in a DMF solution for 10 minutes with microwave irradiation. HBTU (58 µmol) and HOBt (58 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 2 in the form of a freeze-dried powder (22.0 mg, yield 17%).

Synthesis of 5-oxohexanoyl-Gly-Val-Thr-Ser-Ala-Pro-Asp-Thr(Sialyl-T)-Am-Pro-Ala-Pro-Gly-Ser-Thr-Ala-Pro-Pro-Ala-His-Gly-Val-Thr-Cys-NH$_2$ (Compound 9)

Compound 8 (10 mM, 300 µL, water) was mixed with a reaction solution obtained by mixing 1,000 mM HEPES buffer (pH 7.3, 30 µL), 1,000 mM HEPES buffer (pH 7.0, 30 µL), 1,000 mM MnCl$_2$ (6 µL), 150 mM CMP-NeuAc (60 µL), 1.4 U/mL α2,3-(O)-Sialyltransferase, Rat, Recombinant, S. frugiperda (30 µL, Calbiochem), and water (74 µL). The mixture was incubated for 24 hours at 25° C., after which the reaction liquid was purified by reverse-phase high-performance liquid chromatography, yielding Compound 9 in the form of a freeze-dried powder (5.5 mg, 60% yield).

Synthesis of 5-oxohexanoyl-Pro-Pro-Thr-Thr-Thr-Pro-Ser-Pro-Pro-Pro-Thr-Ser-Thr-Thr-Thr-Leu-Pro-Pro-Thr-NH$_2$ (Compound 10)

A peptide solid phase was synthesized using a solid phase support in the form of Rink Amide-ChemMatrix resin (0.48 mmol/g, 25 mg, 12 μmol, a product of Biotage). The amino acid extension reaction was conducted under conditions of microwave irradiation (40 W, 2,450 MHz, 50° C.) by reacting Fmoc amino acid derivative (48 μmol), HBTU (48 μmol), HOBt (48 μmol) and DIEA (72 μmol) in a DMF solution for 9 minites. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 1 hour with trifluoroacetic acid:water:triisopropylsilane (95:2.5:2.5, v/v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 10 in the form of a freeze-dried powder (7.2 mg, yield 30%).

Synthesis of 5-oxohexanoyl-Pro-Pro-Thr-Thr(Tn)-Thr(Tn)-Pro-Ser-Pro-Pro-Pro-Thr-Ser-Thr-Thr(Tn)-Thr(Tn)-Leu-Pro-Pro-Thr-NH$_2$ (Compound 11)

A glycopeptide solid phase was synthesized using a solid phase support in the form of Rink Amide-ChemMatrix resin (0.48 mmol/g, 25 mg, 12 μmol). The amino acid extension reaction was conducted under conditions of microwave irradiation (40 W, 2,450 MHz, 50° C.) by reacting Fmoc amino acid derivative (48 μmol), HBTU (48 μmol), HOBt (48 μmol) and DIEA (72 μmol) in a DMF solution for 9 minutes. The sugar chain substitution amino acid extension reaction was conducted by reacting Fmoc-Thr (Ac3GalNacα)-OH] (14 μmol), PyBOP (14 μmol), and HOBt (14 μmol) and DIEA (36 μmol) in a DMF solution for 10 minutes with microwave irradiation. PyBOP (14 μmol) and HOBt (14 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water:triisopropylsilane (95:2.5:2.5, v/v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 11 in the form of a freeze-dried powder (4.7 mg, yield 14%).

Synthesis of 5-oxohexanoyl-Val-Glv-Pro-Leu-Tvr-Ser-Glv-Cvs-Am-Leu-Thr(Tn)-Leu-Leu-Arg-Pro-Glu-Lys-His-Gly-Ala-Ala-NH, (Compound 12)

A glycopeptide solid phase was synthesized using a solid phase support in the form of Rink Amide-ChemMatrix resin (0.48 mmol/g, 50 mg, 24 μmol). The amino acid extension reaction was conducted under conditions of microwave irradiation (40 W, 2,450 MHz, 50° C.) by reacting Fmoc amino acid derivative (96 μmol), HBTU (96 μmol), in a DMF solution of HOBt (96 μmol) and DIEA (144 μmol) for 9 minutes. The sugar chain substitution amino acid extension reaction was conducted by reacting Fmoc-Thr (Ac3GalNacα)-OH] (28 μmol), PyBOP (28 μmol), and HOBt (28 μmol) and DIEA (72 μmol) in a DMF solution for 10 minutes with microwave irradiation. PyBOP (28 μmol) and HOBt (28 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 1 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 12 in the form of a freeze-dried powder (9.0 mg, yield 15%).

Example 1 Synthesis of Compound 3

Synthesis of 5-oxohexanoyl-Ser-Ala-Ser-Thr-Gly-His-Ala-Thr(Tn)-Pro-Leu-Pro-Val-Thr-Asp-Thr-Ser-Cys-NH$_2$ (Compound 3)

A peptide solid phase was synthesized using a solid phase support in the form of TentaGel S RAM resin (0.24 mmol/g, 200 mg, 48 μmol, obtained from Rapp Polymere, GmbH). The amino acid extension reaction was conducted under conditions of microwave irradiation (40 W, 2,450 MHz, 50° C.) by reacting Fmoc amino acid derivative (192 μmol), HBTU (192 μmol), HOBt (192 μmol) and DIEA (288 μmol) in a DMF solution for six minutes. The sugar chain substitution amino acid extension reaction was conducted by reacting Fmoc-Thr(Ac3GalNacα)-OH (58 μmol), HBTU (58 μmol), and HOBt (58 μmol) and DIEA (144 μmol) in a DMF solution for 10 minutes with microwave irradiation. HBTU (58 μmol) and HOBt (58 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups.

Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 3 in the form of a freeze-dried powder (13.0 mg, yield 14%).

Summary of identification data of Compounds 1 to 12:
MALDI-TOFMS spectrum of glycopeptide derived from MUC4: FIG. 1
(a) Compound 1, m/z calcd for $C_{73}H_{181}N_{20}O_{28}S$ $[M+Na]^+$ 1777.804, found 1777.910;
(b) Compound 2, m/z calcd for $C_{81}H_{131}N_{21}O_{33}S$ $[M+Na]^+$ 1980.884, found 1980.994;
(c) Compound 3, m/z calcd for $C_{81}H_{131}N_{21}O_{33}S$ $[M\ Na]^+$ 1980.884, found 1981.045;
(d) Compound 4, m/z calcd for $C_{81}H_{131}N_{21}O_{33}S$ $[M+Na]^+$ 1980.884, found 1981.054;
(e) Compound 5, m/z calcd for $C_{81}H_{131}N_{21}O_{33}S$ $[M+Na]^+$ 1980.884, found 1980.996.

Figure 2:
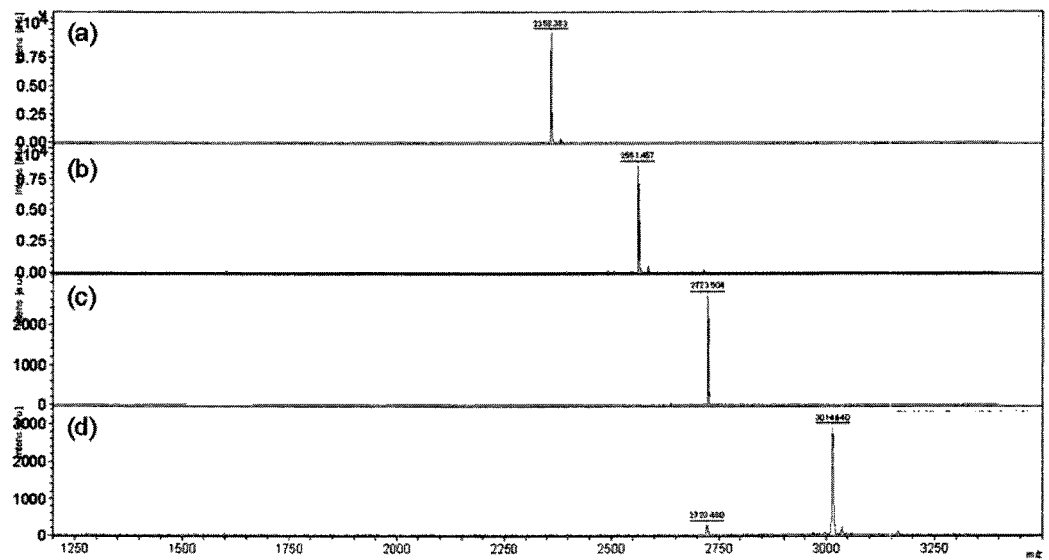
FIG. 2 The MALDI-TOFMS spectrum of an MUC1-derived glycopeptide.

MALDI-TOFMS spectrum of glycopeptide derived from MUC1: FIG. 2
(a) Compound 6, m/z calcd for $C_{100}H_{160}N_{30}O_{34}S$ $[M+H]^+$ 2358.151, found 2358.383;
(b) Compound 7, m/z calcd for $C_{108}H_{173}N_{31}O_{39}S$ $[M+H]^+$ 2561.231, found 2561.457;
(c) Compound 8, m/z calcd for $C_{114}H_{183}N_{31}O_{44}S$ $[M+H]^+$ 2723.283, found 2723.504;
(d) Compound 9, m/z calcd for $C_{125}H_{200}N_{32}O_{52}S$ $[M+H]^+$ 3014.379, found 3014.640.

Figure 3:
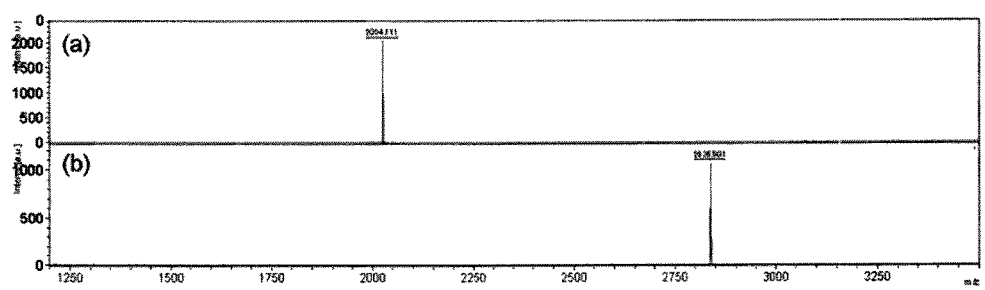
FIG. 3 The MALDI-TOFMS spectrum of an MUC2-derived glycopeptide.

MALDI-TOFMS spectrum of glycopeptide derived from MUC2: FIG. 3
(a) Compound 10, m/z calcd for $C_{90}H_{144}N_{20}O_{31}$ $[M+Na]^+$ 2024.020, found 2024.111;
(b) Compound 11, m/z calcd for $C_{122}H_{196}N_{24}O_{51}$ $[M+Na]^+$ 2836.338, found 2836.501.

Figure 4:
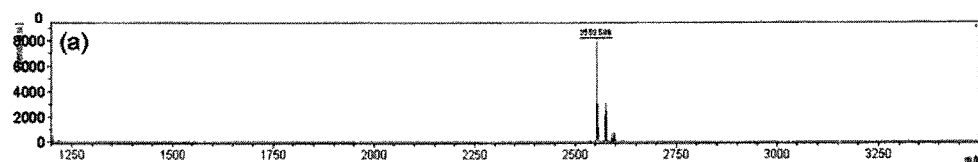
FIG. 4 The MALDI-TOFMS spectrum of an MUC16-derived glycopeptide.

MALDI-TOFMS spectrum of glycopeptide derived from MUC16: FIG. 4
(a) Compound 12, m/z calcd for $C_{113}H_{187}N_{32}O_{33}S$ $[M+H]^+$ 2552.366, found 2552.588.

Example 2

Preparation of Monoclonal Antibody Employing Ser-Ala-Ser-Thr-Gly-his-Ala-Thr(Tn)-Pro-Leu-Pro-Val-Thr-Asp-Thr-Ser as Antigen Compound Ser-Ala-Ser-Thr-Gly-His-Ala-Thr(Tn)-Pro-Leu-Pro-Val-Thr-Asp-Thr-Ser-Cys-NH$_2$ (85 µg), obtained by adding Cys required for binding carrier protein to N-terminal of Ser-Ala-Ser-Thr-Gly-His-Ala-Thr(Tn)-Pro-Leu-Pro-Val-Thr-Asp-Thr-Ser, was conjugated with keyhole limpet hemocyanin (KLH) and administered to the tail base of BDF(Registered trademark)-1 mice to induce an immune response. The same method was employed 17 hours later to conduct additional immunization with Compound 3. Blood was collected 3 days later and the iliac lymph nodes were collected. The cells collected were fused with myeloma SP2 cells. The hybridomas were cultured in HAT selective medium, and the antibody-producing cells were selected. Next, the hybridoma culture supernatant was seeded onto an ELISA plate and screened in a binding reaction with Compound 3.

Fused cell cloning was conducted by the limiting dilution method. Hybridoma strains 2D5-2E12 (Patent Microorganisms Depository (NPMD), National Institute of Technology and Evaluation (NITE), Accession No. NITE BP-01774), 2D5-1E7 (NPMD Accession No. NITE BP001775), 3G8-2D10 (NPMD Accession No. NITE BP-01776), and 4A9-2B6 (NPMD Accession No. NITE BP001777) producing the targeted monoclonal antibodies SN-01, SN-02, SN-03, and SN-04, respectively, were established.

Example 3 Culturing Cell Strains Producing Monoclonal Antibodies (SN-01, SN-02, SN-03, or SN-04) and Obtaining Purified Antibodies Culturing method: SN-01 producing hybridoma strain 2D5-2E12 was grown in RPMI-1640 medium containing 10% fetal bovine serum (FBS). A 22 mL quantity of the serum-free medium Panserin H4000 (PAN-Biotech) was added to the $8.1 \times 10^6$ cells recovered to obtain a suspension. The cells were cultured to acclimate them to the medium. The acclimated cells were grown to about $1.0 \times 10^8$ in the same medium and subcultured to $5.0 \times 10^5$/mL. This was then statically cultured for 2 weeks, at which point the culture supernatant was removed by centrifugation. Each of hybridoma strains 2D5-1E7, 3G8-2D10, and 4A9-2B6 was cultured by the same method.

Purification method: SN-01 to 04 was purified by the method given below from the hybridoma strains 2D5-2E12, 2D5-1E7, 3G8-2D10, and 4A9-2B6, respectively, that had been cultured. A 200 mL quantity of culture supernatant was passed through a 0.45 µm filter to obtain a purified antibody material. Alternatively, ammonium sulfate was added to the culture supernatant to achieve 50% saturation, and 10,000 g was centrifuged for 20 minutes to collect the precipitate. This was dissolved in 10 mL of PBS, the solution was dialyzed to obtain a purified material, and this was subjected to affinity chromatography employing a HiTrap Protein G HP column (GE Healthcare). A HiTrap Protein G HP column connected after an ÄKTA Explorer 100 (GE Healthcare) was equilibrated with 20 mM sodium phosphate buffer (pH 7.0), and the culture supernatant was added. Unneeded components that had not bound to the column were washed away with the same buffer, after which antibodies were eluted by a small quantity of 0.1 M glycine-HCl buffer (pH 2.5) and neutralized by the addition of a small quantity of 1 M tris-HCl buffer (pH 9.0). The fractions that passed through the column were repeatedly added to the column to increase the collection yield of antibodies. The operations up to this point yielded 0.65 mg of SN-01, 1.1 mg of SN-02, 0.3 mg of SN-03, and 1.1 mg of SN-04.

Example 4 Reaction Specificity Evaluation of Antibodies

Preparation of Array of Immobilized Glycopeptide

A substrate for an immobilized sugar chain array (made by Sumitomo Bakelite) was treated for 2 hours at 37° C. with 2 M HCl and the t-butoxycarbonyl group (Boc group) protection was removed. The product was washed twice with water and then dried to place aminoxy groups on the surface of the substrate. A spotting solution (25 mM AcOH/ pyridine, 0.005% Triton X-100, pH 5.4) was added to the various synthetic glycopeptides shown in Table 1 to dissolve them. A spotter (BioChip Arrayer, made by Cartesion) employed a spot pin (CMP, pin diameter 0.4 mm, Arraylt Corp.) to spot the substrate. A reaction was conducted for 1 hour at 80° C. to immobilize the glycopeptides on the substrate. Washing was conducted once with water, the product was immersed in 10 mg/mL succinic anhydride, a reaction was conducted for 3 hours at room temperature, and the unreacted aminooxy groups were protected. Washing was conducted twice with water and the product was dried.

Figures 1, 5:
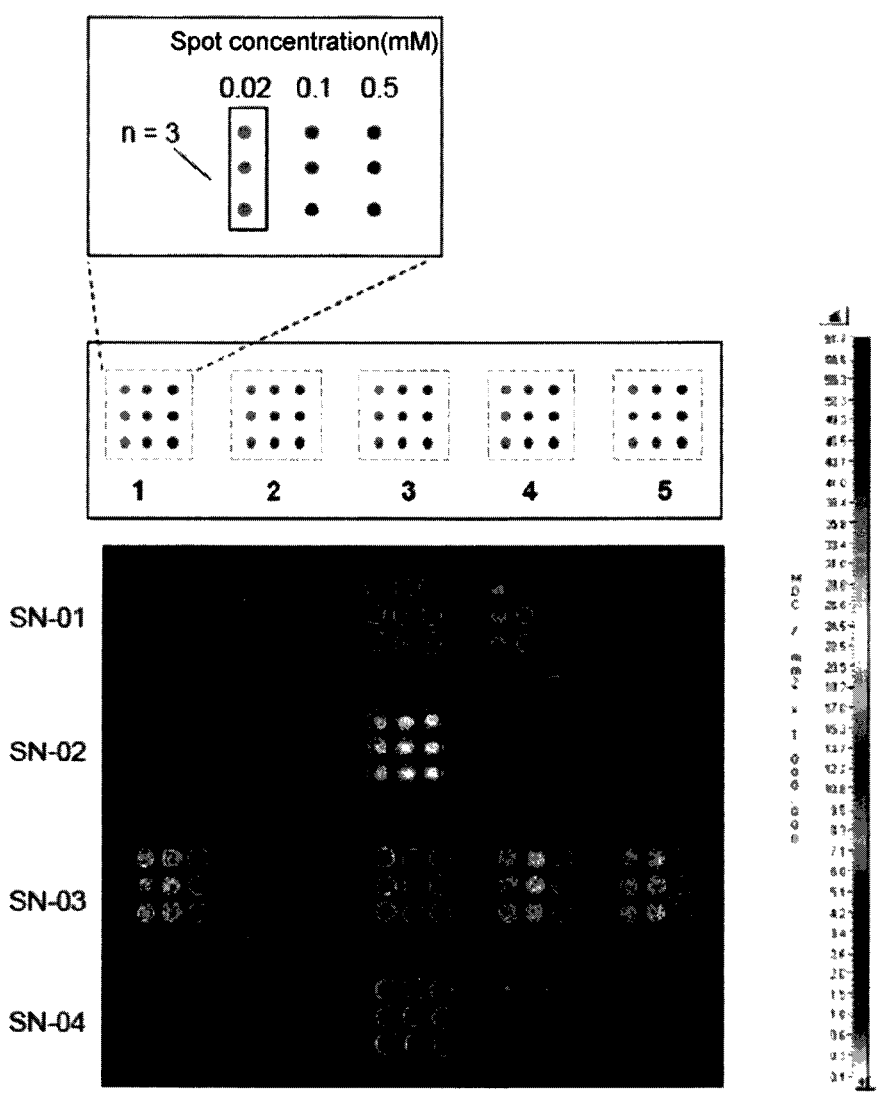
Figure 5:
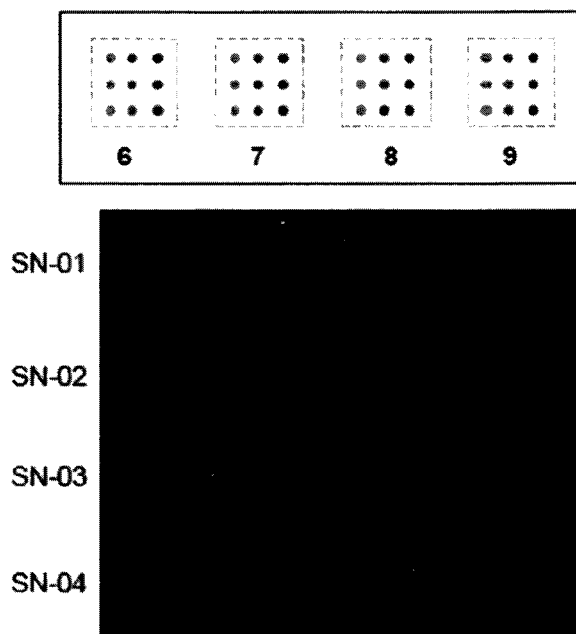
Figure 2:
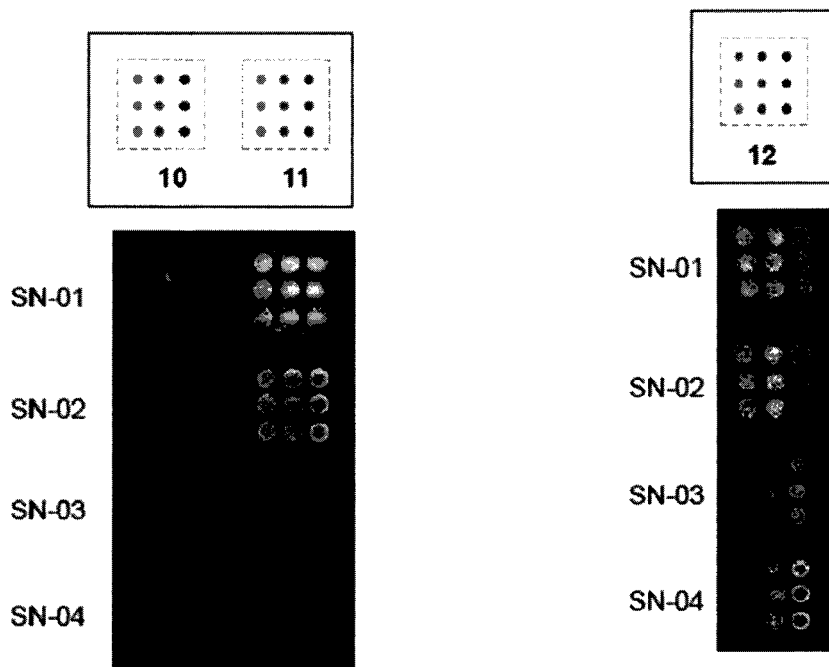
Figure 6:
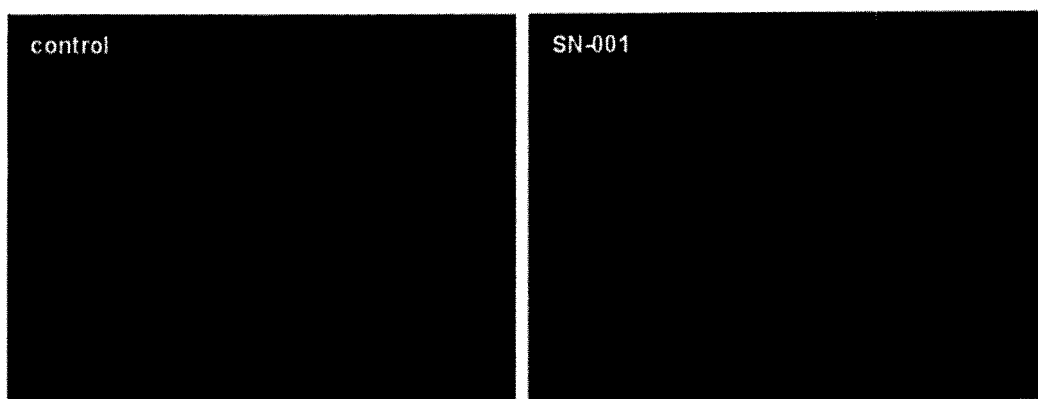
FIG. 6 Immunofluorescent stained image of pancreatic cancer cell BxPC-3 accumulation by SN-01 obtained in Example 6.

The reaction supernatant was diluted 10-fold with the reaction solution given below. A Hybricover (made by Sumitomo Bakelite) was placed on the immobilized glycopeptide array, 70 µL of the diluted solution was spread out, and a reaction was conducted for 2 hours at room temperature. The Hybricover was removed and the substrate was washed one time each with cleansing solution and water to clean it. The substrate was dried, the Hybricover was positioned, and Anti-IgG(H+L), mouse, goat-poly, and Cy3 (Rockland Immunochemicals) prepared in 1 µg/mL with the following solutions were seeded on the substrate. These were reacted for 1 hour at room temperature. Following the reaction, the product was washed with cleansing solution. Fluorescent intensity of Cy3 was measured with a scanner (Typhoon TRIO+, GE Healthcare. A fluorescent response digital image was created with Array Vision™ software (GE Healthcare). The results are given in FIG. 5.

Reaction solution: 50 mM Tris.HCl (pH 7.4), 100 mM NaCl, 1 mM $CaCl_2$, $MnCl_2$, $MgCl_2$, 0.05% Tween 20
Cleansing solution: 50 mM Tris.HCl (pH 7.4), 100 mM NaCl, 1 mM $CaCl_2$, $MnCl_2$, $MgCl_2$, 0.05% Triton X-100 peptides derived from MU4. These antibodies exhibited unique patterns such as the following in their reactions with the various glycopeptides.

SN-01 was:
i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen;
ii) not binding to Ser-Ala-Ser-Thr-Gly-His-Ala-Thr-Pro-Leu-Pro-Val-Thr-Asp-Thr-Ser (naked peptide SEQ ID NO:2), and to glycopeptides in which Tn is modified at a different position from the glycopeptide employed as antigen;
iii) strongly binding to a glycopeptide in which Tn is modified with tandem unit peptides in the form of MUC2 and MUC16; and
iv) not binding to a glycopeptide in which Tn is modified with an MUC1 tandem unit peptide.

SN-02 was:
i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen;
ii) not binding to (naked peptide SEQ ID NO:2) and to glycopeptides in which Tn is modified at a different position from the glycopeptide employed as antigen;
iii) binding to a glycopeptide in which Tn is modified with tandem unit peptides in the form of MUC2 and MUC16; and
iv) not binding to a glycopeptide in which Tn is modified with an MUC1 tandem unit peptide.

SN-03 was:
i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen;

TABLE 1

Sequence data of MUC4-derived glycopeptide 3 employed as immunogen and analogs thereof (sequences bound to crosslinking ketone and Cys)

| MUC type | Compound no. | Sequence (N→C) |
| --- | --- | --- |
| MUC4 | 1 | 5-oxohexanoyl-Ser-Ala-Ser-Thr-Gly-His-Ala-Thr-Pro-Leu-Pro-Val-Thr-Asp-Thr-Ser-Cys-NH2 |
|  | 2 | 5-oxohexanoyl-Ser-Ala-Ser-Thr(Tn)-Gly-His-Ala-Thr-Pro-Leu-Pro-Val-Thr-Asp-Thr-Ser-Cys-NH2 |
|  | 3 | 5-oxohexanoyl-Ser-Ala-Ser-Thr-Gly-His-Ala-Thr(Tn)-Pro-Leu-Pro-Val-Thr-Asp-Thr-Ser-Cys-NH2 |
|  | 4 | 5-oxohexanoyl-Ser-Ala-Ser-Thr-Gly-His-Ala-Thr-Pro-Leu-Pro-Val-Thr(Tn)-Asp-Thr-Ser-Cys-NH2 |
|  | 5 | 5-oxohexanoyl-Ser-Ala-Ser-Thr-Gly-His-Ala-Thr-Pro-Leu-Pro-Val-Thr-Asp-Thr(Tn)-Ser-Cys-NH2 |
| MUC1 | 6 | 5-oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-Cys-$NH_2$ |
|  | 7 | 5-oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-Cys-$NH_2$ |
|  | 8 | 5-oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-Cys-$NH_2$ |
|  | 9 | 5-oxohexanoyl-Gly-Val-Thr-Ser-Ala-Pro-Asp-Thr(Sialyl-T)-Arg-Pro-Ala-Pro-Gly-Ser-Thr-Ala-Pro-Pro-Ala-His-Gly-Val-Thr-Cys-$NH_2$ |
| MUC2 | 10 | 5-oxohexanoyl-Pro-Pro-Thr-Thr-Thr-Pro-Ser-Pro-Pro-Pro-Thr-Ser-Thr-Thr-Thr-Leu-Pro-Pro-Thr-$NH_2$ |
|  | 11 | 5-oxohexanoyl-Pro-Pro-Thr-Thr(Tn)-Thr(Tn)-Pro-Ser-Pro-Pro-Pro-Thr-Ser-Thr-Thr(Tn)-Thr(Tn)-Leu-Pro-Pro-Thr-$NH_2$ |
| MUC16 | 12 | 5-oxohexanoyl-Val-Gly-Pro-Leu-Tyr-Ser-Gly-Cys-Arg-Leu-Thr(Tn)-Leu-Leu-Arg-Pro-Glu-Lys-His-Gly-Ala-Ala-$NH_2$ |

Characteristics of Antibodies SN-01 to 04
Antibodies SN-01 to 04 specifically recognized and bound to the sugar chain core structure of antigen glycoii) binding to both (naked peptide SEQ ID NO:2) and to glycopeptides in which Tn is modified at a different position from the glycopeptide employed as antigen; and iii) not binding to a glycopeptide in which Tn is modified with a tandem unit peptide in the form of MUC1, MUC2, or MUC16.

SN-04 was:

i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen ii) not binding to (naked peptide SEQ ID NO:2) and to glycopeptides in which Tn is modified at a different position from the glycopeptide employed as antigen;

iii) either not binding or binding weakly to a glycopeptide in which Tn is modified with a tandem unit peptide in the form of MUC1, MUC2, or MUC16.

Example 5 Detection of MUC4 Glycopeptides in Patient Serum

An examination was conducted into whether the antigen peptides would be detected in pancreatic cancer, ovarian cancer, and lung cancer specimen serum using SN-01, SN-03, and SN-04. The number of specimens was 5 to 10 serum samples from patients who had been clearly clinically diagnosed with the disease and several normal serum samples as negative controls. No antigen glycopeptides were detected in the normal serum but antigen glycopeptides were detected in the patient serum samples.

Accumulation of the Antibodies in MUC4 Expression Cells Based on Immunofluorescent Chromosomes To each of the wells on an 8-well chamber slide were added $9.6 \times 10^3$ pancreatic cancer cells BxPC-3 that had been suspended in RPMI-1640 (10% FBS) and the cells were cultured for 16 hours at 37° C. in a 5% $CO_2$ atmosphere. The medium was aspirated off and 4% cold methanol in PBS was added to immerse the cells in about 2 mm. The cells were immobilized for about 15 minutes. The immobilization solution was aspirated off, and the wells were washed three times with PBS, five minutes each time. Blocking was conducted for 1 hour with blocking buffer (PBS containing 5% BSA). The blocking solution was aspirated off, the corresponding antibodies were added, and the mixture was incubated overnight at 4° C. The antibodies were aspirated off, after which the wells were washed three times with PBS, five minutes each time. Cy™5 labeled anti-mouse IgG antibody was added and the mixture was incubated for 1 hour at room temperature in a dark room. The secondary antibodies were aspirated off, after which the wells were washed three times with PBS, five minutes each time. Observation with a BZ-9000 (KEYENCE) all-in-one fluorescence microscope, revealed staining of the cell surfaces.

Example 7 Cell Proliferation Blocking Test

Figure 7:
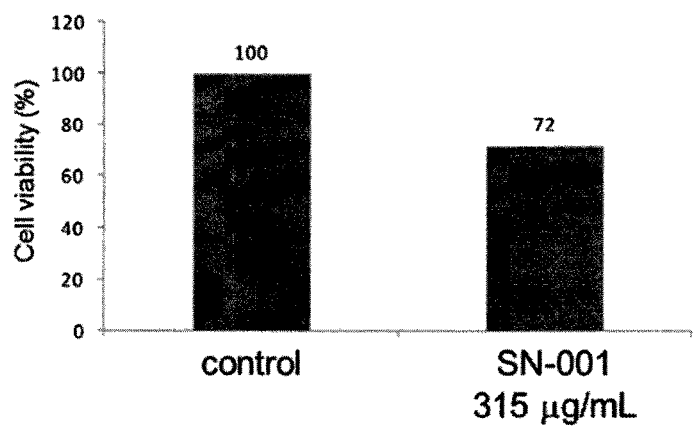
FIG. 7 Shows the results of cell proliferation suppression (suppression of proliferation of breast cancer cells OCUB-M by SN-01) test obtained in Example 7.

To each well in a 96-well PrimeSurface® (Sumitomo Bakelite) were added 100 μL of breast cancer cells OCUB-M (1,000 cells/well) and 10 mL (34.7 mg) of SN-001 (34.7 mg/mL). The cells were cultured for 96 hours at 37° C. in a 5% CO2 atmosphere. Cell Titer 96® Aqueous One Solution Proliferation Reagent (Promega) was added and culturing was conducted for another 1.5 hours. The number of live cells was then determined by the 490 nm absorbance with a SpectraMaxM5 (Molecular Devices). The results are given in FIG. 7. The number of live ovarian cells OCUB-M cultured in the presence of SN-001 was found to be 28% less than the number of live cells cultured in the absence of SN-01.

Example 8 Test of Blocking the Binding of Galectin 3

To each well of an 8-well chamber slide were added $4.8 \times 10^3$ pancreatic cancer cells BxPC-3 suspended in RPMI-1640 (10% FBS) and the cells were cultured for 16 hours at 37° C. in a 5% $CO_2$ atmosphere. The medium was aspirated off and 4% formaldehyde in PBS was added to immerse the cells in about 2 mm. The cells were immobilized for 15 minutes. The immobilization solution was aspirated off, and the wells were washed three times with PBS, five minutes each time. Blocking was conducted for 1 hour with blocking buffer (PBS containing 5% BSA). The blocking solution was aspirated off. The antibody alone and mixtures of various concentrations of the antibody and galectin 3 were prepared. These were incubated for 2 hours at 4° C. The antibodies were aspirated off, after which the wells were washed three times with PBS, five minutes each time. Cy5 labeled anti-mouse IgG antibody was added and the mixtures were incubated for 1 hour at room temperature in a dark room. The secondary antibodies were aspirated off, after which the wells were washed three times with PBS, five minutes each time. Observation with a BZ-9000 (KEYENCE) all-in-one fluorescence microscope revealed blocking of the binding of galectin 3 and MUC4 dependent on the antibody concentration.

Figure 8:
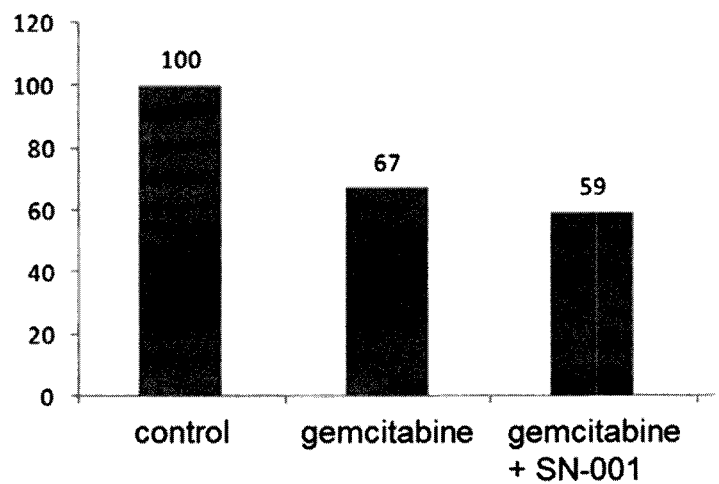
FIG. 8 Shows the results of pancreatic cancer cell proliferation suppression test combining SN-01 and gemcitabine obtained in Example 9.

Example 9 Test of Blocking the Proliferation of Cancer Cells in Combination with a Chemotherapeutic Agent (1) Pancreatic Cells To each well of a 96-well plate were added 1×103 cells of pancreatic cancer cells BxPC3 suspended in RPMI-1640 and the cells were cultured for 48 hours at 37° C. in a 5% CO2 atmosphere. After 48 hours, three groups were separated: addition of gemcitabine alone (overall concentration 1 mM), combined use of gemcitabine (overall concentration 1 mM) and SN-001 (overall concentration 0.35 mg/mL), and no addition. The cells were cultured for 48 hours at 37° C. in a 5% CO2 atmosphere. Cell Titer 96® Aqueous One Solution Proliferation Reagent (Promega) was added to each cell and the cells were cultured for another 1.5 hours. The number of live cells was then determined by 490 nm absorbance with a SpectraMaxM5 (Molecular Devices). The results are given in FIG. 8. Blocking of cell proliferation was observed, with the greatest reduction in the number of live cells being found for the combined use of gemcitabine and SN-01 (59% of the control).

(2) Breast Cancer Cells

Figure 9:
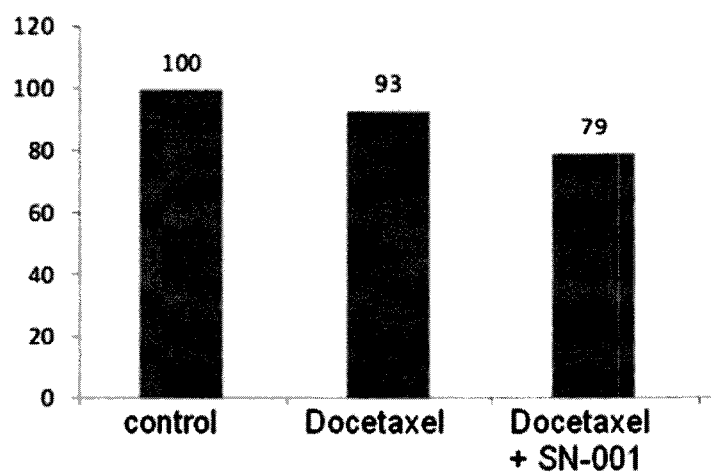
FIG. 9 Shows the results of pancreatic cancer cell proliferation suppression test combining SN-01 and docetaxel obtained in Example 9.

To each well of a 96-well plate were added 1×103 cells of breast cancer cells OCUB-M suspended in RPMI-1640 and the cells were cultured for 48 hours at 37° C. in a 5% CO2 atmosphere. After 48 hours, three groups were separated: addition of docetaxel alone (overall concentration 50 μM), combined use of docetaxel (overall concentration 50 μM) and SN-001 (overall concentration 0.35 mg/mL), and no addition. The cells were cultured for 48 hours at 37° C. in a 5% CO2 atmosphere. Cell Titer 96® Aqueous One Solution Proliferation Reagent (Promega) was added to each well and the cells were cultured for another 1.5 hours. The number of live cells was then determined by 490 nm absorbance with a SpectraMaxM5 (Molecular Devices). The results are given in FIG. 9. Blocking of cell proliferation was observed, with the greatest reduction in the number of live cells being found for the combined use of docetaxel and SN-01 (79% of the control).

INDUSTRIAL APPLICABILITY

The present invention provides antibodies to glycopeptides obtained by sugar chain modification of MUC4 derived peptides to form conformational epitopes. Using the anti-MUC4 antibodies of the present invention, it is possible to reliably and readily detect the presence of MUC4 with high sensitivity for specific conformational epitopes, and to determine malignant tumors as MUC4-associated diseases. The present invention is thus useful in the field of medical diagnosis. Further, the anti-MUC4 antibodies of the present invention are also useful in the field of pharmaceuticals, such as in cancer diagnosis, because they affect the functions of cancer cells relating to MUC4.

SEQUENCE LISTING

SEQ ID NO: 1 Amino acid sequence of tandem unit peptide of human MUC4
SEQ ID NO: 2 Amino acid sequence of peptide with Cys added to C terminal of tandem unit peptide of human MUC4
SEQ ID NO: 3 Amino acid sequence of peptide with Cys added to C terminal of tandem unit peptide of human MUC1
SEQ ID NO: 4 Amino acid sequence of tandem unit peptide of human MUC2
SEQ ID NO: 5 Amino acid sequence of tandem unit peptide of human MUC16

The invention claimed is:

1. A monoclonal antibody having specificity for a glycopeptide comprising a tandem unit peptide of human MUC4 having the amino acid sequence of SEQ ID NO: 1 and an O-linked sugar chain; wherein said O-linked sugar chain is N-acetylgalactosamine (GalNAc)linked to a threonine at the eighth position in SEQ ID NO: 1, wherein said monoclonal antibody is selected from the group consisting of
- SN-01 secreted by a hybridoma registered under Accession No. NITE BP-1774;
- SN-02 secreted by a hybridoma registered under Accession No. NITE BP-1775;
- SN-03 secreted by a hybridoma registered under Accession No. NITE BP-1776 and
- SN-04 secreted by a hybridoma registered under Accession No. NITE BP-1777.

2. A monoclonal antibody as claimed in claim 1, wherein said monoclonal antibody is SN-04 and has binding properties set forth in i) to iii) below:
   i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);
   ii) not binding to a peptide having the amino acid sequence denoted by SEQ ID NO:1, and to glycopeptides having the amino acid sequence denoted by SEQ ID NO:1 in which Tn is modified at a position different from the glycopeptide employed as antigen;
   iii) either not binding or binding weakly to a glycopeptide in which Tn is modified with a tandem unit peptide of MUC1, MUC2, or MUC16.

3. A SN-01 monoclonal antibody as claimed in claim 1 having binding properties set forth in i) to iv) below:
   i) binding strongly to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a 0-linked sugar chain comprised of N-acetylgalactosamine (GalNAc);
   ii) not binding to a peptide having the amino acid sequence denoted by SEQ ID NO:1, and to glycopeptides having the amino acid sequence denoted by SEQ ID NO:1 in which Tn is modified at a position different from the glycopeptide employed as antigen;
   iii) strongly binding to a glycopeptide in which Tn is modified with tandem unit peptides of MUC2 and MUC16; and
   iv) not binding to a glycopeptide in which Tn is modified with an MUC1 tandem unit peptide.

4. The SN-02 monoclonal antibody according to claim 1 having binding properties set forth in i) to iv) below:
   i) binding strongly to the glycopeptide Ser-Ala-Ser-Thr-Gly-His-Ala-(Tn) Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);
   ii) not binding to a peptide having the amino acid sequence denoted by SEQ ID NO:1, and to glycopeptides having the amino acid sequence denoted by SEQ ID NO:1 in which Tn is modified at a position different from the glycopeptide employed as antigen;
   iii) strongly binding to a glycopeptide in which Tn is modified with tandem unit peptides of MUC2 and MUC16; and
   iv) not binding to a glycopeptide in which Tn is modified with an MUC1 tandem unit peptide.

5. A SN-03 monoclonal antibody as claimed in claim 1 having binding properties set forth in i) to iii) below:
   i) strongly binding to the glycopeptide Ser-Ala-Ser-Thr-Gly-His-Ala-(Tn)Thr-Pro-Leu-Pro-Val-Thr-Asp-Thr-Ser derived from MUC4 that is employed as antigen, wherein Tn denotes a O-linked sugar chain comprised of N-acetylgalactosamine (GalNAc);
   ii) binding to both a peptide having the amino acid sequence denoted by SEQ ID NO:1, and to glycopeptides having the amino acid sequence denoted by SEQ ID NO:1 in which Tn is modified at a position different from the glycopeptide employed as antigen; and
   iii) not binding to a glycopeptide in which Tn is modified with a tandem unit peptide of MUC1, MUC2, or MUC16.

6. A method for detecting MUC4 in a human body fluid sample, comprising:
   (a) contacting the sample with the monoclonal antibody according to claim 1; and
   (b) measuring the formation of antibody-MUC4 antigen complex in the sample after contact.

7. The method according to claim 6, for detecting the presence or absence of a malignant tumor in which the overexpression of MUC4 is observed in the body fluid sample.

8. The method according to claim 7, in which the malignant tumor is selected from the group consisting of pancreatic cancer, ovarian cancer, breast cancer, biliary tract cancer, esophageal cancer, colon cancer, and lung cancer.

9. A kit for detecting MUC4 in a human body fluid sample, comprising:
   (a) at least one monoclonal antibody according to claim 1; and
   (b) a reagent for measuring antibody-MUC4-antigen complex.

10. A pharmaceutical composition for treating malignant tumors, containing at least one monoclonal antibody according to claim 1 in a pharmaceutically acceptable liquid.

11. The composition according to claim 10, wherein the malignant tumor is selected from the group consisting of pancreatic cancer, ovarian cancer, breast cancer, biliary tract cancer, esophageal cancer, colon cancer, and lung cancer.

12. The pharmaceutical composition for treating malignant tumors according to claim 10 further comprising a chemotherapeutic agent or molecularly targeted drug as active ingredient.

13. The pharmaceutical composition according to claim 12, wherein the malignant tumor is selected from the group consisting of pancreatic cancer, ovarian cancer, breast cancer, biliary tract cancer, esophageal cancer, colon cancer, and lung cancer.

14. The pharmaceutical composition according to claim 12, wherein the monoclonal antibody and chemotherapeutic agent or molecularly targeted drug are administered separately.

15. A hybridoma cell expressing a monoclonal antibody having specificity for MUC4, deposited with NITE under an Accession No. selected from the group consisting of NITE BP-01777, NITE BP-01774, NITE BP-01775 and NITE BP-01776.

16. A method for treating a MUC4-overexpressing malignant tumor in a subject, the method comprising administering to the subject a therapeutically effective amount of a monoclonal antibody as claimed in claim 1.

* * * * *